(12) United States Patent
Günzburg et al.

(10) Patent No.: US 7,531,353 B1
(45) Date of Patent: *May 12, 2009

(54) NON SELF-INACTIVATING, EXPRESSION TARGETED RETROVIRAL VECTORS

(75) Inventors: Walter Henry Günzburg, Mölding (AT); Robert Michael Saller, München (DE)

(73) Assignee: GSF-Forschungszentrum fur Unwelt und Gesundheit GmbH, Neuherberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 08/808,827

(22) Filed: Feb. 28, 1997

Related U.S. Application Data

(63) Continuation-in-part of application No. PCT/EP95/03445, filed on Sep. 1, 1995.

(30) Foreign Application Priority Data

Sep. 2, 1994 (DK) ..................................... 1017/94

(51) Int. Cl.
C12N 5/10 (2006.01)
C12N 15/00 (2006.01)

(52) U.S. Cl. .................................... 435/325; 435/320.1
(58) Field of Classification Search .................. 514/44; 435/320.1; 536/24.1, 23.5
See application file for complete search history.

(56) References Cited

U.S. PATENT DOCUMENTS

| | | | | |
|---|---|---|---|---|
| 6,117,681 | A * | 9/2000 | Salmons et al. | 435/456 |
| 6,730,511 | B1 * | 5/2004 | Gunzburg et al. | 435/320.1 |
| 7,022,319 | B1 * | 4/2006 | Gunzburg et al. | 424/93.1 |
| 7,074,398 | B1 * | 7/2006 | Gunzburg et al. | 424/93.2 |

FOREIGN PATENT DOCUMENTS

| | | |
|---|---|---|
| EP | 0415731 A2 | 8/1990 |
| EP | 0 779 929 | 4/2001 |
| WO | WO89/11539 | 5/1989 |
| WO | WO94/29437 | 6/1994 |
| WO | WO96/37623 | 5/1996 |

OTHER PUBLICATIONS

Kay et al. In vivo gene therapy of hemophilia B: Sustained partial correction in Factor IX-deficient dogs. Science vol. 262 pp. 117-119, 1993.*
Longmore et al. Both megakaryocytopoiesis and erythropoiesis are induce in mice infected with a retrovirus expressing an oncogenic erythropoietin receptor. Blood vol. 82 pp. 2386-2395, 1993.*
Price et al. Lineage analysis in the vertebrate nervous system by retrovirus-mediated gene transfer. Proc. Natl. Acad. Sci. USA vol. 84 pp. 156-160, 1987.*
Faustinella et al. A new family of murine retroviral vectors with extended multiple cloning sites for gene insertion. Human Gene Therapy vol. 5 pp. 307-312, 1994.*
Mee et al. Constructio and hormone regulation of a novel retroviral vector. Gene vol. 88 pp. 289-292, 1990.*
Panganiban et al. The retrovirus pol gene encodes a product required for DNA integration : Identification of a retrovirus int locus. Proc. Natl. Acad. Sci. USA vol. 81 pp. 7885-7889, 1984.*
Scarpa et al. Characterixation of recombinant helper retroviruses from Moloney-based vectors in ecotropic and amphotropic packaging cell lines. Virology vol. 180 pp. 849-852, 1991.*
Panganiban et al. The terminal nucleotides of retrovirus DNA are required for integration but not virus production. Nature vol. 306 pp. 155-160, 1983.*
Miller et al. Improved retroviral vectors for gene transfer and expression. Biotechniques vol. 7, pp. 980-990, 1989.*
Junker et al., Genetic instability of MoMLV-based antisense double-copy retroviral vector designed for HIV-1 gene therapy, Gene Therapy (1995) pp. 639-646.*
Felder et al, Functional and Biological Properties of an Avian Variant Long Terminal Repeat Containing Multiple A to G Conversions in the U3 Sequence, Aug. 1994, Journal of Virology, pp. 4759-4767.*
Mehigh et al, Development of a Recombinant Bovine Leukemia Virus Vector for Delivery of a Synthetic Bovine Growth Hormone-Releasing Factor Gene into Bovine Cells, Jun. 1992, Journal of Admin. Sci, 71:687-693.*
Scott et al, Promoter-Proximal Poly(A) Sites Are Processed Efficiently, but the RNA Products Are Unstable in the Nucleus, Apr. 1997, Molecular and Cellular Biology, pp. 2127-2135.*
Günzburg, W.H. et. al., *Biologicals*, 23:5-12 (1995).
Couture, L.A. et. al., *Human Gene Therapy*, 5:667-677 (1994).
Miller, A.D. and Rosman, G.J., *BioTechniques*, 7(9):980-990 (1989).
Salmons, B. and Günzburg, W.H., *Human Gene Therapy*, 4:129-141 (1993).
Cannon, P.M. et al., "Murine Leukemia Virus-Based Tat-Inducible Long Terminal Repeat Replacement Vectors: a New System for Anti-Human Immunodeficiency Virus Gene Therapy", *J. of Virology*, 70(11);8234-8240 (1996).
Robinson, D. et al., "Retroviral vector with a CMV-IE/HIV-TAR hybrid LTR gives high basal expression levels and is up-regulated by HIV-1 Tat", *Gene Therapy*, 2:269-278 (1995).

(Continued)

*Primary Examiner*—John S Brusca
(74) *Attorney, Agent, or Firm*—Jenkins, Wilson, Taylor & Hunt, P.A.

(57) ABSTRACT

The present invention relates to a retroviral vector undergoing promoter conversion comprising a 5'LTR region of the structure U3-R-U5; one or more sequences selected from coding and non-coding sequences; and a 3'LTR region comprising a completely or partially deleted U3 region wherein said deleted U3 region is replaced by a polylinker sequence, followed by the R and U5 region. The retroviral vector undergoes promoter conversion and is useful as a gene transfer vehicle for targeted gene therapy.

65 Claims, 16 Drawing Sheets

OTHER PUBLICATIONS

Ferrari, G. et al., "A Retroviral Vector Containing a Muscle-Specific Enhancer Drives Gene Expression Only in Differentiated Muscle Fibers", *Human Gene Therapy*, 6:733-742 (1995).

Vile, R.G. et al., "Tissue-Specific Gene Expression from Mo-MLV Retroviral Vectors with Hybrid LTRs Containing the Murine Tyrosinase Enhancer/Promoter", *Virology*, 214:307-313 (1995).

Guntaka, Transcription of Termination and Polyadenylation in Retroviruses, *Microbiological Review* 57(3):511-521 (Sep. 1993).

Hoke et al., "Expression of Human Adenosine Deaminase from Various Strong Promoters after Gene Transfer into Human Hematopoietic Cell Line," *Blood*, vol. 74, No. 2, pp. 876-881 (Aug. 1, 1989).

Official Action corresponding to Finnish Patent Application No. 970892 dated Mar. 20, 2008.

* cited by examiner

```
                    SacII (art.)         WAP
                   ┌─────────┐   ┌──────────────
(F) 5'-AACCGCGGCCAGGAGAAGTCACCCTCAG-3'
(G) 5'-ACACGCGTCTGCCTCTCCCTCAGGACACA-3'
                   └─────────┘   └──────────────
                    MluI (art.)         WAP
```

FIG. 9

NON SELF-INACTIVATING, EXPRESSION TARGETED RETROVIRAL VECTORS

RELATED APPLICATIONS

This application is a continuation-in-part of International Application No. PCT/EP95/03445, filed Sep. 1, 1995, which claims priority to Danish Application No. 1017/94, filed Sep. 2, 1994.

BACKGROUND OF THE INVENTION

The use of retroviral vectors for gene therapy has received much attention and currently is the method of choice for the transferral of therapeutic genes in a variety of approved protocols both in the USA and in Europe (Kotani et al., Human Gene Therapy 5:19-28 (1994)). However most of these protocols require that the infection of target cells with the retroviral vector carrying the therapeutic gene occurs in vitro, and successfully infected cells are then returned to the affected individual (Rosenberg et al., Hum. Gene Ther. 3:75-90 (1992); for a review see Anderson, W. F., Science 256:808-813 (1992)). Such ex vivo gene therapy protocols are ideal for correction of medical conditions in which the target cell population can be easily isolated (e.g. lymphocytes). Additionally the ex vivo infection of target cells allows the administration of large quantities of concentrated virus which can be rigorously safety tested before use.

Unfortunately, only a fraction of the possible applications for gene therapy involve target cells that can be easily isolated, cultured and then reintroduced. Additionally, the complex technology and associated high costs of ex vivo gene therapy effectively preclude its disseminated use world-wide. Future facile and cost-effective gene therapy will require an in vivo approach in which the viral vector, or cells producing the viral vector, are directly administered to the patient in the form of an injection or simple implantation of retroviral vector producing cells.

This kind of in vivo approach, of course, introduces a variety of new problems. First of all, and above all, safety considerations have to be addressed. Virus will be produced, possibly from an implantation of virus producing cells, and there will be no opportunity to precheck the produced virus. It is important to be aware of the finite risk involved in the use of such systems, as well as trying to produce new systems that minimize this risk.

Retroviral vector systems consist of two components (FIG. 1):

1) the retroviral vector itself is a modified retrovirus (vector plasmid) in which the genes encoding for the viral proteins have been replaced by therapeutic genes and marker genes to be transferred to the target cell. Since the replacement of the genes encoding for the viral proteins effectively cripples the virus it must be rescued by the second component in the system which provides the missing viral proteins to the modified retrovirus.

The second component is:

2) a cell line that produces large quantities of the viral proteins, however lacks the ability to produce replication competent virus. This cell line is known as the packaging cell line and consists of a cell line transfected with a second plasmid carrying the genes enabling the modified retroviral vector to be packaged.

To generate the packaged vector, the vector plasmid is transfected into the packaging cell line. Under these conditions the modified retroviral genome including the inserted therapeutic and marker genes is transcribed from the vector plasmid and packaged into the modified retroviral particles (recombinant viral particles). This recombinant virus is then used to infect target cells in which the vector genome and any carried marker or therapeutic genes becomes integrated into the target cell's DNA. A cell infected with such a recombinant viral particle cannot produce new vector virus since no viral proteins are present in these cells. However the DNA of the vector carrying the therapeutic and marker genes is integrated in the cell's DNA and can now be expressed in the infected cell.

The essentially random integration of the proviral form of the retroviral genome into the genome of the infected cell (Varmus, Science 240:1427-1435 (1988)) led to the identification of a number of cellular proto-oncogenes by virtue of their insertional activation (Varmus, Science 240:1427-1435 (1988); van Lohuizen and Berns, Biochim. Biophys. Acta, 1032:213-235 (1990)). The possibility that a similar mechanism may cause cancers in patients treated with retroviral vectors carrying therapeutic genes intended to treat other pre-existent medical conditions has posed a recurring ethical problem. Most researchers would agree that the probability of a replication defective retroviral vector, such as all those currently used, integrating into or near a cellular gene involving in controlling cell proliferation is vanishingly small. However it is generally also assumed that the explosive expansion of a population of replication competent retrovirus from a single infection event, will eventually provide enough integration events to make such a phenotypic integration a very real possibility.

Retroviral vector systems are optimized to minimize the chance of replication competent virus being present. However it has been well documented that recombination events between components of the retroviral vector system can lead to the generation of potentially pathogenic replication competent virus and a number of generations of vector systems have been constructed to minimize this risk of recombination (reviewed in Salmons and Gunzburg, Human Gene Therapy 4:129-141 (1993)).

A further consideration when considering the use of in vivo gene therapy, both from a safety stand point and from a purely practical stand point, is the targeting of retroviral vectors. It is clear that therapeutic genes carried by vectors should not be indiscriminately expressed in all tissues and cells, but rather only in the requisite target cell. This is especially important if the genes to be transferred are toxin genes aimed at ablating specific tumor cells. Ablation of other, nontarget cells would obviously be very undesirable.

A number of retroviral vector systems have been previously describes that should allow targeting of the carried therapeutic genes (Salmons and Gunzburg, Human Gene Therapy 4:129-141 (1993)). Most of these approaches involve either limiting the infection event to predefined cell types or using heterologous promoters to direct expression of linked heterologous therapeutic or marker genes to specific cell types. Heterologous promoters are used which should drive expression of linked genes only in the cell type in which this promoter is normally active. These promoters have previously been inserted, in combination with the marker or therapeutic gene, in the body of the retroviral vectors, in place of the gag, pol or env genes.

The retroviral Long Terminal Repeat (LTR) flanking these genes carries the retroviral promoter, which is generally non-specific in that it can drive expression in many different cell types (Majors, Curr. Tops. In Micro. Immunol. 157:49-92 (1990)). Promoter interference between the LTR promoter, and heterologous internal promoters, such as the tissue specific promoters described above has been reported. Additionally, it is known that retroviral LTRs harbor strong enhancers that can, either independently, or in conjunction with the retroviral promoter, influence expression of cellular genes near the site of integration of the retrovirus. This mechanism has been shown to contribute to tumorigenicity in animals (van Lohuizen and Berns Biochim. Biophys. Acta, 1032:213-235 (1990)). These two observations have encouraged the development of Self-Inactivating-Vectors (SIN) in which retroviral promoters are functionally inactivated in the target cell (PCT WO94/29437). Further modifications of these vectors include the insertion of promoter gene cassettes within the LTR region to create double copy vectors (PCT WO89/11539). However, in both these vectors the heterologous promoters inserted either in the body of the vector, or in the LTR region are directly linked to the marker/therapeutic gene.

The previously described SIN vector mentioned above carrying a deleted 3'LTR(PCT WO94/29437) utilize in addition a strong heterologous promoter such as that of Cytomegalovirus (CMV), instead of the retroviral 5' LTR promoter (U3-free 5'LTR) to drive expression of the vector construct in the packaging cell line. A heterologous polyadenylation signal is also included in the 3'LTR (PCT WO94/29437).

SUMMARY OF THE INVENTION

The present invention relates to retroviral vectors including a vector which undergoes promoter conversion (ProCon vectors such as, for example, the BAG vector). The vector system is useful as a gene transfer vehicle for targeted gene therapy.

In particular, the present invention relates to a retroviral vector which is capable of undergoing promoter conversion comprising a 5' long terminal repeat (LTR) region of the structure U3-R-U5; one or more sequences selected from coding and non-coding sequences; and a 3' LTR region comprising a completely or partially deleted U3 region wherein said deleted U3 region is replaced by a polylinker sequence, followed by the R and U5 region. The LTR regions can be selected from at least one element of, for example, Murine Leukaemia Virus, Mouse Mammary Tumor Virus, Murine Sarcoma Virus, Simian Immunodeficiency Virus, Human Immunodeficiency Virus, Human T Cell Leukaemia Virus, Feline Immunodeficiency Virus, Feline Leukaemia Virus, Bovine Leukaemia Virus, and Mason-Pfizer-Monkey Virus.

In one embodiment, the polylinker sequence of the retroviral vector of the present invention comprises at least one unique restriction site. In another embodiment, the polylinker sequence comprises at least one insertion of a heterologous DNA fragment (e.g., regulatory elements and promoters). In a particular embodiment of the present invention, the regulatory elements and promoters of the heterologous DNA are target cell specific in their expression. In addition, the regulatory elements and promoters of the retroviral vector can regulate the expression of at least one of the coding sequences of the retroviral vector. The regulatory elements can also be regulatable by transacting molecules. In another embodiment, the heterologous DNA is DNA homologous to one or more cellular sequences or a part thereof.

The coding sequences of the retroviral vector of the present invention can be, for example, sequences coding for marker genes, therapeutic genes, antiviral genes, antitumor genes, and cytokine genes. In another embodiment, at least one of the coding sequences for a retroviral protein (e.g., a retroviral protein involved in integration) is altered or at least partially deleted in the retorviral vector of the present invention.

The present invention also relates to a retroviral vector system comprising a retroviral vector which is capable of undergoing promoter conversion comprising a 5' LTR region of the structure U3-R-U5; one or more sequences selected from coding and non-coding sequences; and a 3' LTR region comprising a completely or partially deleted U3 region wherein said deleted U3 region is replaced by a polylinker comprising regulatory sequences, followed by the R and U5 region; and a packaging cell line (e.g., psi-2, psi-Crypt, psi-AM, GP+E-86, PA317 and GP+envAM-12) harboring at least one retroviral or recombinant retroviral construct coding for proteins required for said retroviral vector to be packaged. In one embodiment, the packaging cell line harbors retroviral or recombinant retroviral constructs coding for those retroviral proteins which are not encoded in the retroviral vector.

The present invention also relates to a method for introducing homologous or heterologous nucleotide sequences (e.g., genes or parts of genes encoding for proteins, regulatory sequences and promoters) into target human or animal cell populations in vitro and in vivo comprising infecting the target cell population with recombinant retroviruses produced by the retroviral vector system of the present invention. In a particular embodiment, introduction of homologous or heterologous nucleotide sequences into target human or animal cell populations in vitro and in vivo is accomplished by infecting the target cell population with recombinant retrovirus particles of the present invention.

The present invention also relates to a recombinant retroviral particle(s) obtained by transfecting a packaging cell line of a retroviral vector system of the present invention, and culturing the cells under suitable conditions.

The present invention also relates to a retroviral provirus produced by infection of target cells with a recombinant retroviral particle of the present invention whereby the polylinker in the 3' LTR becomes duplicated during the process of reverse transcription in the target cell and appears in the 5' LTR as well as in the 3' LTR of the resulting provirus.

The present invention also relates to mRNA of the retroviral provirus of the present invention. In addition, the invention relates to RNA of a retroviral vector of the present invention. The present invention also relates to a pharmaceutical composition containing a therapeutically effective amount of a recombinant retroviral particle of the present invention.

BRIEF DESCRIPTION OF THE FIGURES

FIG. 9 are the primer F(SEQ ID NO:6), and G(SEQ ID NO:7) used to construct pWAPBAG.

DETAILED DESCRIPTION OF THE INVENTION

Figure 1:
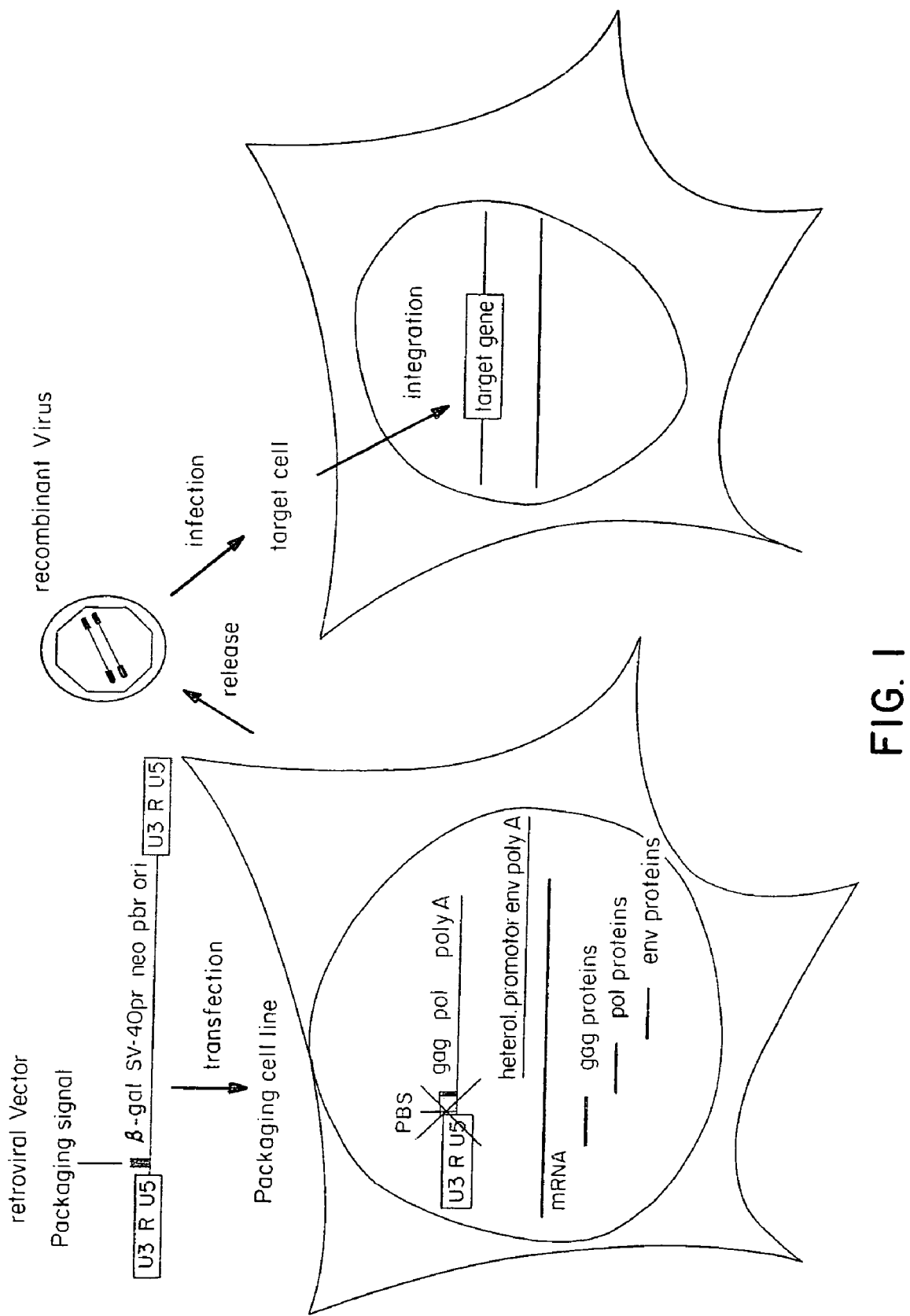
FIG. 1 is a graphic representation of a retroviral vector system.

The object of the present invention is the construction of a novel retroviral vector which can be used as a safe gene transfer vehicle for targeted gene therapy with a reduced probability to undergo recombination with the packaging construct. This novel vector carries heterologous promoter and/or regulatory elements in the 3'LTR which, after infection become duplicated and translocated to the 5'LTR in the target cell, eventually controlling expression of marker/therapeutic genes, not directly linked to the promoter, but rather inserted into the body of the vector. This vector does not undergo self-inactivation—but instead promoter exchange, giving rise to the name ProCon for Promoter Conversion.

Since Promoter Conversion does not result in Self-Inactivation, the retroviral vector will be transcriptionally active in the target cell. However both LTRs will consist to a large extent of heterologous promoter/enhancer sequences in the target cell. This will reduce the likelihood of the integrated vector in the target cell being subject to the same inactivation over long periods as has been described for conventional vectors (Xu et al., *Virology* 171:331-341 (1989)) and also will reduce the chance of recombination with endogenous retroviral sequences to generate potentially pathogenic replication competent virus, increasing the safety of the system.

In this invention the 5'LTR of the retroviral vector construct is not modified, and expression of the viral vector in the packaging cells is driven by the normal retroviral U3 promoter. Normal retroviral polyadenylation is allowed, and no heterologous polyadenylation signals are included in the 3'LTR. This is important for the development of in vivo gene therapy strategies, since the normal physiological regulation of the virus, through the normal viral promoter, and possibly also involving the normal viral control of polyadenylation, will prevail over long periods in vivo whilst the packaging cells are producing recombinant virus.

A further modification of this novel retroviral vector foresees the inclusion of cellular sequences instead of the heterologous promoter and/or regulatory elements. This should allow higher selectivity for site specific recombination with cellular sequences to target the integration of retroviral vectors to particular sites in the host cell genome (Saller, R. M., "Design von Locus-und Gewebespezischen Retroviralen Vektoren Ruer Eine In Vivo Gentherapie, Doctoral thesis, Ludwigs-Maximilians University Munich, Germany, (1994)).

To achieve the foregoing and other objects, the invention provides a retroviral vector undergoing promoter conversion comprising a 5'LTR region of the structure U3-R-US; one or more sequences selected from coding and non-coding sequences; and a 3'LTR region comprising a completely or partially deleted U3 region wherein said deleted U3 region is replaced by a polylinker sequence, followed by the R and U5 region.

Said polylinker sequence carries at least one unique restriction site and contains preferably at least one insertion of a heterologous DNA fragment. Said heterologous DNA fragment is preferably selected of regulatory elements and promoters, preferably being target cell specific in their expression, but may also be a DNA fragment with no regulatory function.

Said heterologous DNA fragment is preferably homologous to one or more cellular sequences. The regulatory elements and promoters are preferably regulatable by transacting molecules.

Further objects, features and advantages will be apparent from the following description of preferred embodiments of the invention.

The target cell specific regulatory elements and promoters are selected from one or more elements of the group consisting of Whey Acidic Protein (WAP), Mouse Mammary Tumor Virus (MMTV), β-lactoglobulin and casein specific regulatory elements and promoters, pancreas specific regulatory elements and promoters including carbonic anhydrase II and β-glucokinase regulatory elements and promoters, lymphocyte specific regulatory elements and promoters including immunoglobulin and MMTV lymphocytic specific regulatory elements and promoters and MMTV specific regulatory elements and promoters conferring responsiveness to glucocorticoid hormones or directing expression to the mammary gland. Said regulatory elements and promoters regulate preferably the expression of at least one of the coding sequences of said retroviral vector. The LTR regions are selected from at least one element of the group consisting of LTRs of Murine Leukaemia Virus (MLV), Mouse Mammary Tumor Virus (MMTV), Murine Sarcoma Virus (MSV), Simian Immunodeficiency Virus (SIV), Human Immunodeficiency Virus (HIV), Human T-cell Leukemia Virus (HTLV), Feline Immunodeficiency Virus (FIV), Feline Leukemia Virus (FELV), Bovine Leukemia Virus (BLV) and Mason-Pfizer-Monkey virus (MPMV).

The retroviral vector is based preferably either on a BAG vector (Price et al., *Proc. Natl. Acad. Sci. USA* 84:156-160 (1987)) or an LXSN vector (Miller and Rosman, *Biotechniques* 7:980-990 (1989)).

The coding sequence is preferably selected from one or more elements of the group consisting of marker genes, therapeutic genes, antiviral genes, antitumor genes, and cytokine genes.

Said marker and therapeutic genes are preferably selected from one or more elements of the group consisting of β-galactosidase gene, neomycin gene, Herpes Simplex Virus thymidine kinase gene, puromycin gene, cytosine deaminase gene, hygromycin gene, secreted alkaline phosphatase gene, guanine phosphoribosyl transferase (gpt) gene, alcohol dehydrogenase gene and hypoxanthine phosphoribosyl transferase (HPRT) gene.

Another embodiment of the invention envisages the alteration or partial deletion of at least one retroviral sequence required for integration of retroviruses.

In a further embodiment of the invention a retroviral vector system is provided comprising a retroviral vector as described above as a first component and a packaging cell line harboring at least one retroviral or recombinant retroviral construct coding for proteins required for said retroviral vector to be packaged.

The packaging cell line harbors retroviral or recombinant retroviral constructs coding for those retroviral proteins which are not encoded in said retroviral vector. The packaging cell line is preferably selected from an element of the group consisting of psi-2, psi-Crypt, psi-AM, GP+E-86, PA317 and GP+envAM-12, or of any of these supertransfected with recombinant constructs allowing expression of surface proteins from other enveloped viruses.

Another embodiment of the invention involves the use of a packaging cell line harboring a recombinant retroviral construct defective in integrase function.

After introducing the retroviral vector of the invention as described above in a retroviral packaging cell line and infection of a target cell, as described above, a retroviral provirus is provided wherein said polylinker and any sequences inserted in said polylinker in the 3'LTR become duplicated during the process of reverse transcription in the infected target cell and appear in the 5'LTR as well as in the 3'LTR of the resulting provirus.

The invention includes also mRNA of a retroviral provirus according to the invention and any RNA resulting from a retroviral vector according to the invention.

A further embodiment of the invention provides non-therapeutical method for introducing homologous and/or heterologous nucleotide sequences into human or animal cells in vitro and in vivo comprising transfecting a packaging cell line of a retroviral vector system according to the invention with a retroviral vector according to the invention and infecting a target cell population with recombinant retroviruses produced by the packaging cell line. The nucleotide sequences are selected from one or more elements of the group consisting of genes or parts of genes encoding for proteins, regulatory sequences and promoters.

The retroviral vector, the retroviral vector system and the retroviral provirus as well as RNA thereof is used for producing a pharmaceutical composition for gene therapy in mammals including humans. Furthermore, they are used for targeted integration in homologous cellular sequences.

Promoter Conversion

The present invention uses the principle of promoter conversion typical for retroviruses.

Figure 2:
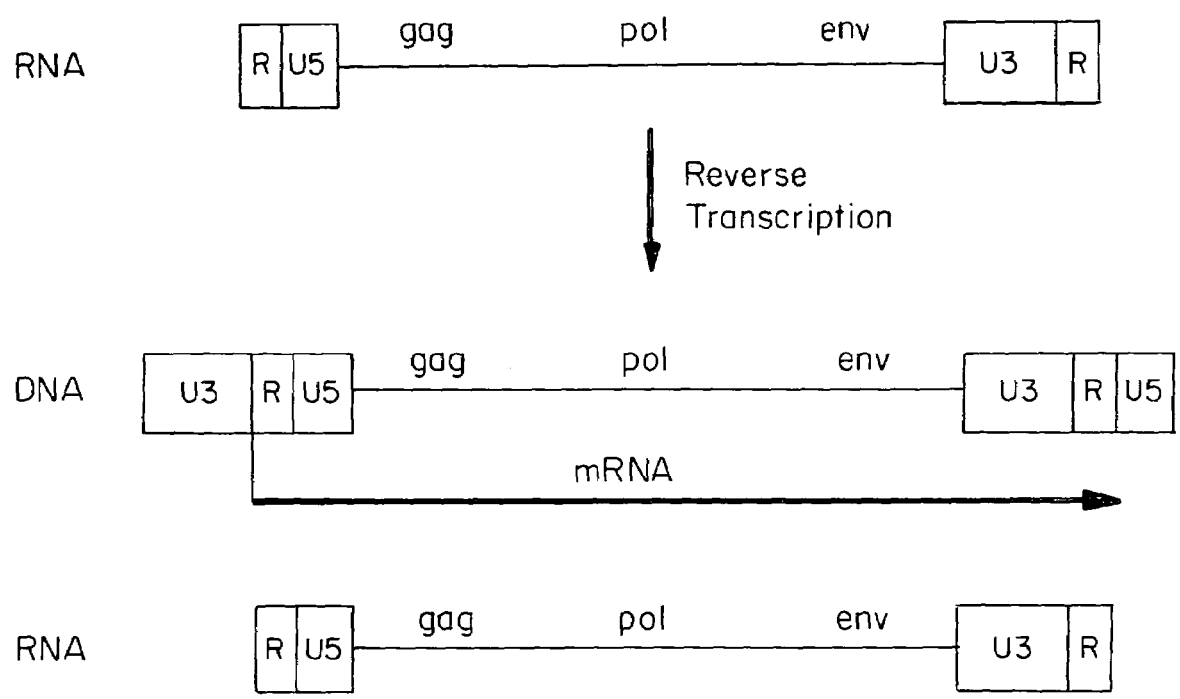
FIG. 2 is a graphic representation of reverse transcription of the retroviral genome.

The retroviral genome consists of an RNA molecule with the structure R-U5-gag-pol-env-U3-R (FIG. 2). During the process of reverse transcription, the U5 region is duplicated and placed at the right hand end of the generated DNA molecule, while the U3 region is duplicated and placed at the left hand end of the generated DNA molecule (FIG. 2). The resulting structure U3-R-U5 is called LTR (Long Terminal Repeat) and is thus identical and repeated at both ends of the DNA structure or provirus (Varmus, *Science* 240:1427-1435 (1988)). The U3 region at the left hand end of the provirus harbors the promoter (see below). This promoter drives the synthesis of an RNA transcript initiating at the boundary between the left hand U3 and R regions and terminating at the boundary between the right hand R and U5 region (FIG. 2). This RNA is packaged into retroviral particles and transported into the target cell to be infected. In the target cell the RNA genome is again reverse transcribed as described above.

Figure 3:
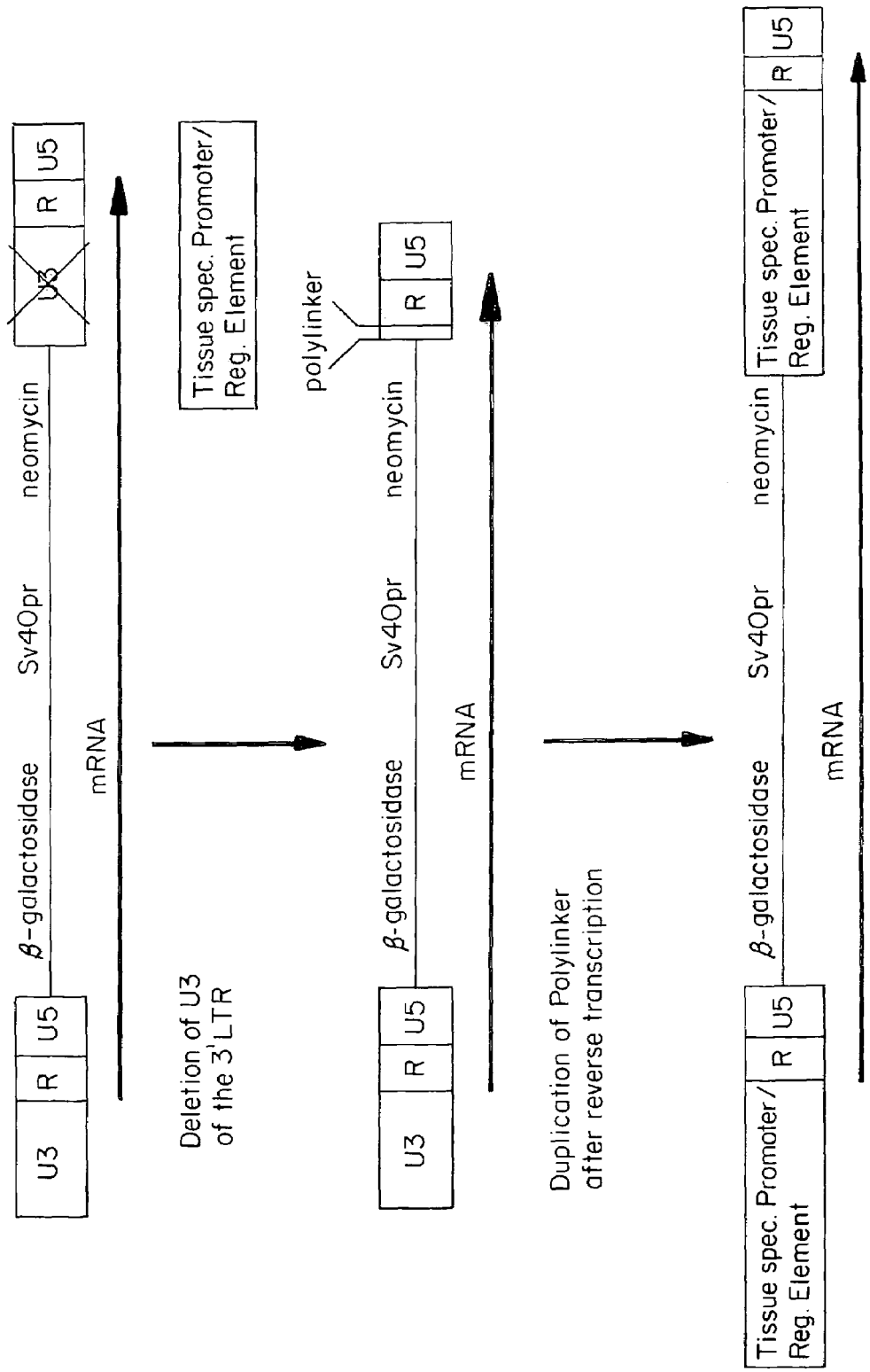
FIG. 3 is a graphic representation of the ProCon

According to the invention, a retroviral vector is constructed in which the right-hand U3 region is altered (FIG. 3), but the normal left-hand U3 structure is maintained (FIG. 3); the vector can be normally transcribed into RNA utilizing the normal retroviral promoter located within the left-hand U3 region (FIG. 3). However the generated RNA will only contain the altered right-hand U3 structure. In the infected target cell, after reverse transcription, this altered U3 structure will be placed at both ends of the retroviral structure (FIG. 3).

If the altered region carries a polylinker (see below) instead of the U3 region then any promoter, including those directing tissue specific expression such as the WAP promoter (see below) can be easily inserted. This promoter will then be utilized exclusively in the target cell for expression of linked genes carried by the retroviral vector. Alternatively or additionally, DNA segments homologous to one or more cellular sequences can be inserted into the polylinker for the purposes of gene targeting, by homologous recombination (see below).

According to the invention, the term "polylinker" is used for a short stretch of artificially synthesized DNA which carries a number of unique restriction sites allowing the easy insertion of any promoter or DNA segment. The term "heterologous" is used for any combination of DNA sequences that is not normally found intimately associated in nature.

Gene expression is regulated by promoters. In the absence of promoter function a gene will not be expressed. The normal MLV retroviral promoter is fairly unselective in that it is active in most cell types (Majors, *Curr. Tops. In Micro. Immunol.* 157:49-92 (1990)). However a number of promoters exist that show activity only in very specific cell types. Such tissue-specific promoters will be the ideal candidates for the regulation of gene expression in retroviral vectors, limiting expression of the therapeutic genes to specific target cells.

In the packaging cell line, the expression of the retroviral vector is regulated by the normal unselective retroviral promoter contained in the U3 region (FIG. 3). However, as soon as the vector enters the target cell promoter conversion occurs, and the therapeutic or marker gene, e.g., β-galactosidase are expressed from a tissue specific promoter of choice introduced into the polylinker (FIG. 3). Not only can virtually any tissue specific promoter be included in the system, providing for the selective targeting of a wide variety of different cell types, but additionally, following the conversion event, the structure and properties of the retroviral vector no longer resembles that of a virus. This, of course, has extremely important consequences from a safety point of view, since ordinary or state-of-the-art retroviral vectors readily undergo genetic recombination with the retroviral packaging construct and/or endogenous retroviruses to produce potentially pathogenic viruses. Promoter conversion (ProCon) vectors do not resemble retroviruses because they no longer carry U3 retroviral promoters after conversion thus reducing the possibility of genetic recombination.

The retroviral promoter structure is carried within the U3 region of the LTR. LTRs carry signals that allow them to integrate into the genome of the target cell. The integration of retroviral proviruses can also contribute to pathogenic changes (van Lohuizen and Berns, *Biochim. Biophys. Acta*, 1032:213-235 (1990)). In one embodiment of the invention ProCon vectors can carry modified LTRs that no longer carry the signals required for integration. Again this increases the potential safety of these vector systems.

Gene Targeting

According to another aspect of the present invention, the retroviral vector is used for targeted integration into the target cell. The integration of the proviral DNA version of the retroviral genome into the target cell is a major advantage to the use of retroviruses as vectors when compared to other viruses such as adenoviruses, since it allows long term stable expression of transferred genes.

However, the random nature of this integration event also poses a major disadvantage to the use of retroviral vectors since it raises the possibility of insertional (in)activation of cellular tumor suppressor genes or proto-oncogenes and thus tumor induction (van Lohuizen and Berns, *Biochim. Biophys. Acta*, 1032:213-235 (1990)).

Homologous recombination has been successfully used to target the integration of transfected or microinjected DNA to specific DNA loci and is routinely used in the construction of "knock-out" transgenic mice or animals (reviewed in Capecchi, *Science* 244:1288-1292 (1989); Bradley et al., *Biotechnology* 10; 534-539 (1992); Morrow and Kucherlapati, *Current Opinion in Biotechnology* 4:577-582 (1993)). Unfortunately, the efficiency of DNA transfer by such purely physical methods is extremely low. In contrast, retroviral mediated gene transfer is very efficient, almost 100% of a population of cells being infectable. A combination of retroviral gene transfer with homologous recombination should allow the construction of an ideal system for locus targeted integration.

We have investigated the feasibility of introducing long homologous pieces of DNA into retroviral vectors in different locations to promote integration by homologous recombination (Saller, R. M., "Design von Locus-und Gewebespezischen Retroviralen Vektoren Ruer Eine In Vivo Gentherapie, Doctoral thesis, Ludwigs-Maximilians University Munich, Germany, (1994)). Both gene conversion and homologous recombination have been evaluated. Using a cell line carrying a single copy of the HSV-tk gene as a target, we have been able to disrupt the target at frequencies 15 fold higher than previously reported by others (Ellis and Bernstein, *Mol. Cell. Biol.* 9:1621-1627 (1989)). Cloning of the recombined fragments of DNA has revealed the presence of both target tk sequence and retroviral vector (Saller, R. M., "Design von Locus-und Gewebespezischen Retroviralen Vektoren Ruer Eine In Vivo Gentherapie, Doctoral thesis, Ludwigs-Maximilians University Munich, Germany, (1994)).

For targeted integration, DNA segments homologous to cellular sequences are inserted into the polylinker of the Pro-Con vectors. After infection of the target cell and reverse transcription, these sequences will appear at the 5' terminal end of the provirus. Terminal homologies have been shown to favor homologous recombination (Bradley, *Curr. Opin. Biotechnol* 2:823-829 (1991)) to isogenic cellular sequences (Bradley, *Curr. Opin. Biotechnol* 2:823-829 (1991)). Infection of target cells which carry mutated versions of the homologous sequence should result in the recombination and thus repair of the mutated sequence. Either just the homologous sequences will recombine into the cellular genome, or the complete vector will be inserted (Saller, R. M., "Design von Locus-und Gewebespezischen Retroviralen Vektoren Ruer Eine In Vivo Gentherapie, Doctoral thesis, Ludwigs-Maximilians University Munich, Germany, (1994)). Not only has this vector class potential for use in gene repair, it can also be utilized to direct the integration of retroviral vectors carrying therapeutic genes to specific loci in the genome which are known not to harbor active genes. This will reduce considerably the possibility of insertional activation or inactivation as described above, and will thus contribute to the safety of the use of retroviral vectors.

The recombinant DNA methods employed in practicing the present invention are standard procedures, well known to those skilled in the art, and described in detail, for example, in "Molecular Cloning" (Sambrook et al., *Molecular Cloning*, Cold Spring Harbor Laboratory Press, New York, USA, (1989) and in "A Practical Guide to Molecular Cloning"; Perbal, B., "A Practical Guide to Molecular Cloning, John Wiley & Sons, 1984)).

The following examples will illustrate the invention further. These examples are however in no way intended to limit the scope of the present invention as obvious modifications will be apparent, and still other modifications and substitutions will be apparent to anyone skilled in the art.

EXAMPLE 1

Mammary Gland Specific Expression After Infection with ProCon Vectors Carrying Mammary Specific Promoters Deletion of the U3 Region and Insertion of a Polylinker In the murine leukemia virus (MLV) retroviral vector known as BAG (Price et al., *Proc. Natl. Acad. Sci. USA* 84:156-160 (1987)) β-galactosidase gene is driven by the promiscuous (i.e., non-tissue specific) MLV promoter in the U3 region of the LTR (FIG. 3). According to the present invention a derivative of the BAG vector has been constructed in which the MLV promoter (U3) located within the 3'LTR, except the inverted repeat, has been deleted by PCR and replaced by a polylinker. The BAG vector lacking the U3 is expressed from the MLV promoter (U3) within the 5'LTR when introduced into a packaging cells line. As a result of the rearrangements occurring the retroviral genome during its life cycle, following infection of its target cell, the polylinker will be duplicated at both ends of the retroviral genome as described in WO-A1-9607748. Thereby a retroviral vector can be constructed in which the expression of the β-galactosidase gene of BAG will be controlled by any heterologous promoter inserted into the polylinker.

As a template for PCR we used pBAGN as plasmid carrying a derivative of the BAG construct carrying only one LTR, created by an NheI digest of the original pBAG followed by a self-ligation of the 7018bp fragment.

Figure 4:
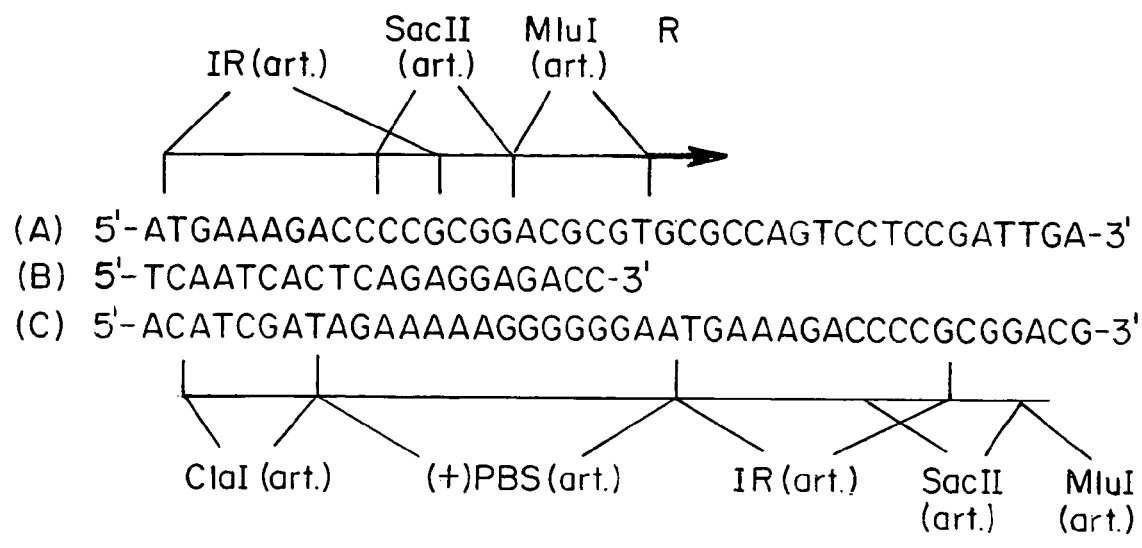
FIG. 4 are the primers A(SEQ ID NO:1), B(SEQ ID NO:2), and C(SEQ ID NO:3) used to construct the BAG vector.
Figure 5:
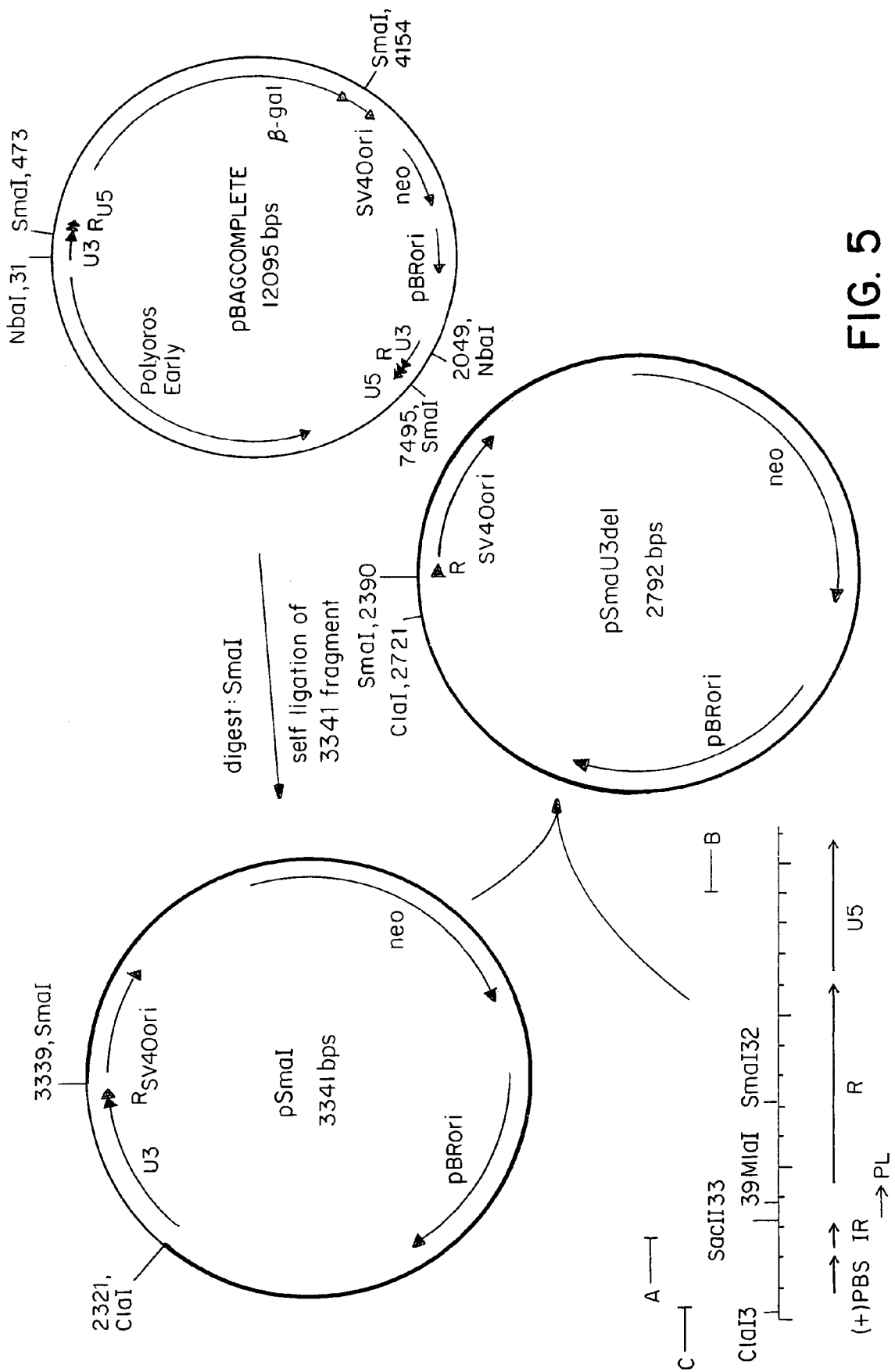
FIG. 5 is a graphic representation of construction of plasmid pSmaU3del.
Figure 6:
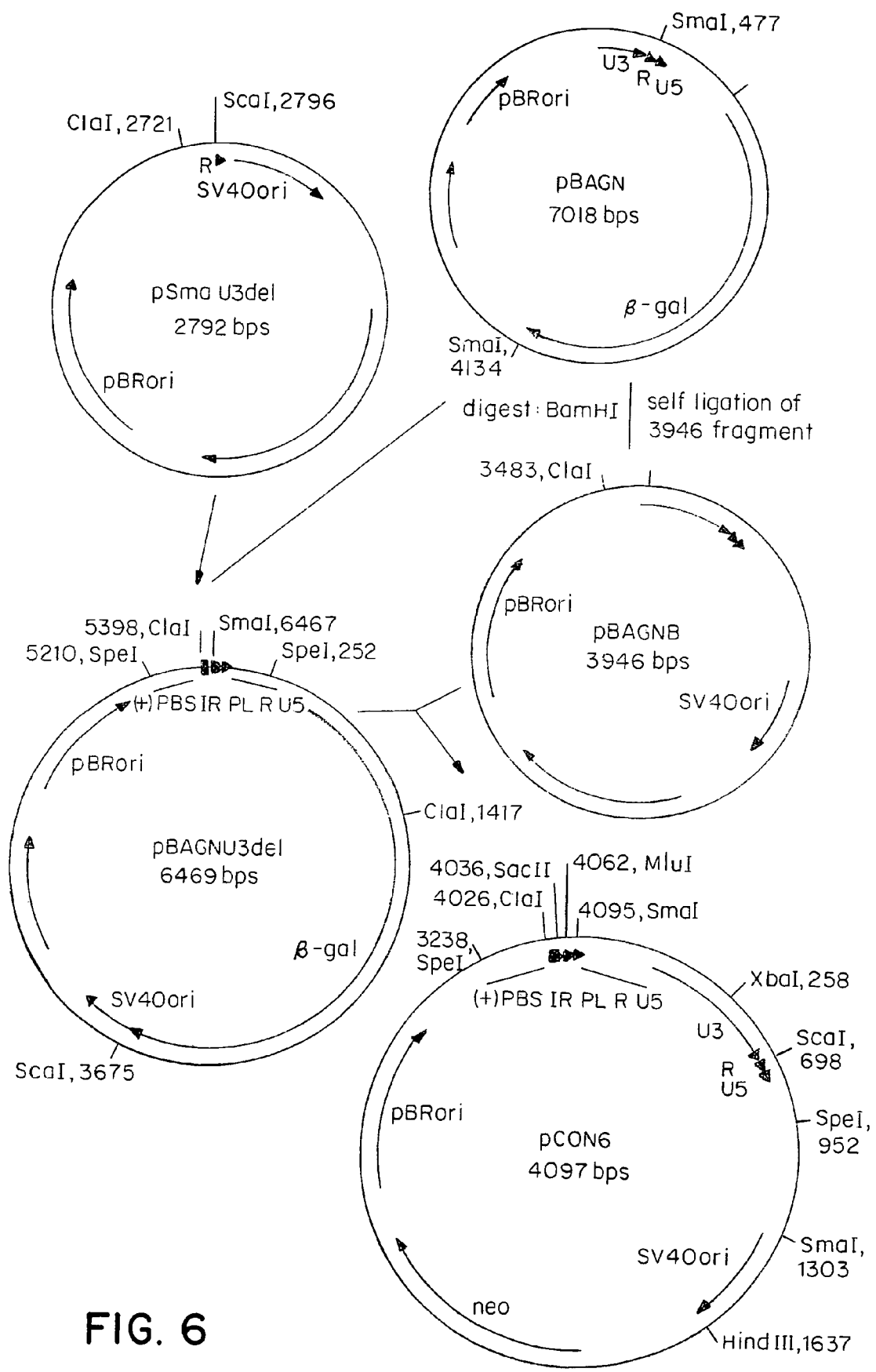
FIG. 6 is a graphic representation of construction of plasmid pCON6.

The 3' end of primer A is complementary to the R-region of the LTR (FIG. 4). The 5'-extension contains an artificial (art) polylinker and an artificial inverted repeat (IR(art.)). Primer B is complementary to the U5 region of the LTR (FIG. 4). After 35 cycles of annealing at 47° C. and extension at 60° C., a 140 bp product was obtained, which was used as a template for the second PCR. In this reaction a ClaI site and an artificial (+)PBS was added 5' of the IR-region using primer C (FIG. 4) in combination with primer B. Annealing was carried out at 53° C. and extension at 72° C. After 35 cycles a 163 bp product was obtained, which was digested with ClaI and SmaI and ligated to a 2722 bp ClaI/SmaI fragment of pSmaI (FIG. 5). The resulting plasmid pSmaU3del (2792 bp) was linearized by a SmaI digest and ligated to a 3677 bp SmaI fragment of pBAGN (FIG. 6) to give the plasmid pBAGNU3del (6369 bp). Deletion of the U3 region was confirmed by sequencing from the ClaI-site into the U5-region using pSmaU3del as template. A ClaI/SpeI (322 bp) fragment containing the U3 deleted LTR was ligated to a ClaI/NheI fragment of pBAGNB (created by self ligation of a 3946 bp fragment of pBAGN) to give the plasmid pCON6 (4097 bp) (FIG. 6). This plasmid carrying a full U3-minus retroviral vector was used as a basis for further cloning.

According to the principle set forth above the following specific promoters have been inserted into the polylinker region or the modified BAG vector: several subregions of the Mouse Mammary Tumor Virus (MMTV) promoter, including a region that confers responsiveness to glucocorticoid hormones and a region containing an element that directs expression to the mammary gland; the Whey Acidic Protein (WAP) promoter. This promoter controls the expression of WAP so that it is only produced in the mammary glands of pregnant and lactating rodents.

Cloning of pMMTVgal

The Mouse Mammary Tumour Virus (MMTV) U3-Region (mtv-2) without the inverted repeats includes a region that confers responsiveness to glucocorticoid hormones and a region containing an element that directs expression to the mammary gland.

The U3 region of MMTV was amplified by PCR using the plasmid pBG102 (a plasmid containing the 3' LTR from mtv 2) as template with primers D and E.

Figure 7:
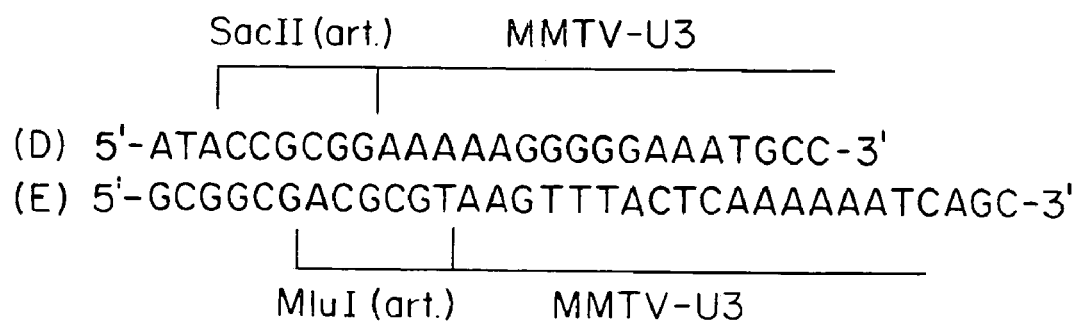
FIG. 7 are the primers D(SEQ ID NO:4), and E(SEQ ID NO:5) used to construct pMMTVgal.

The 3' end of primer D is complementary of the 5' end of MMTV U3 region and carries a SacII site in its 5' extension (FIG. 7). The 3' end of primer E is complementary to the 3' end of the MMTV U3 region and has a Mlul site in its 5' extension (FIG. 7).

Figure 8:
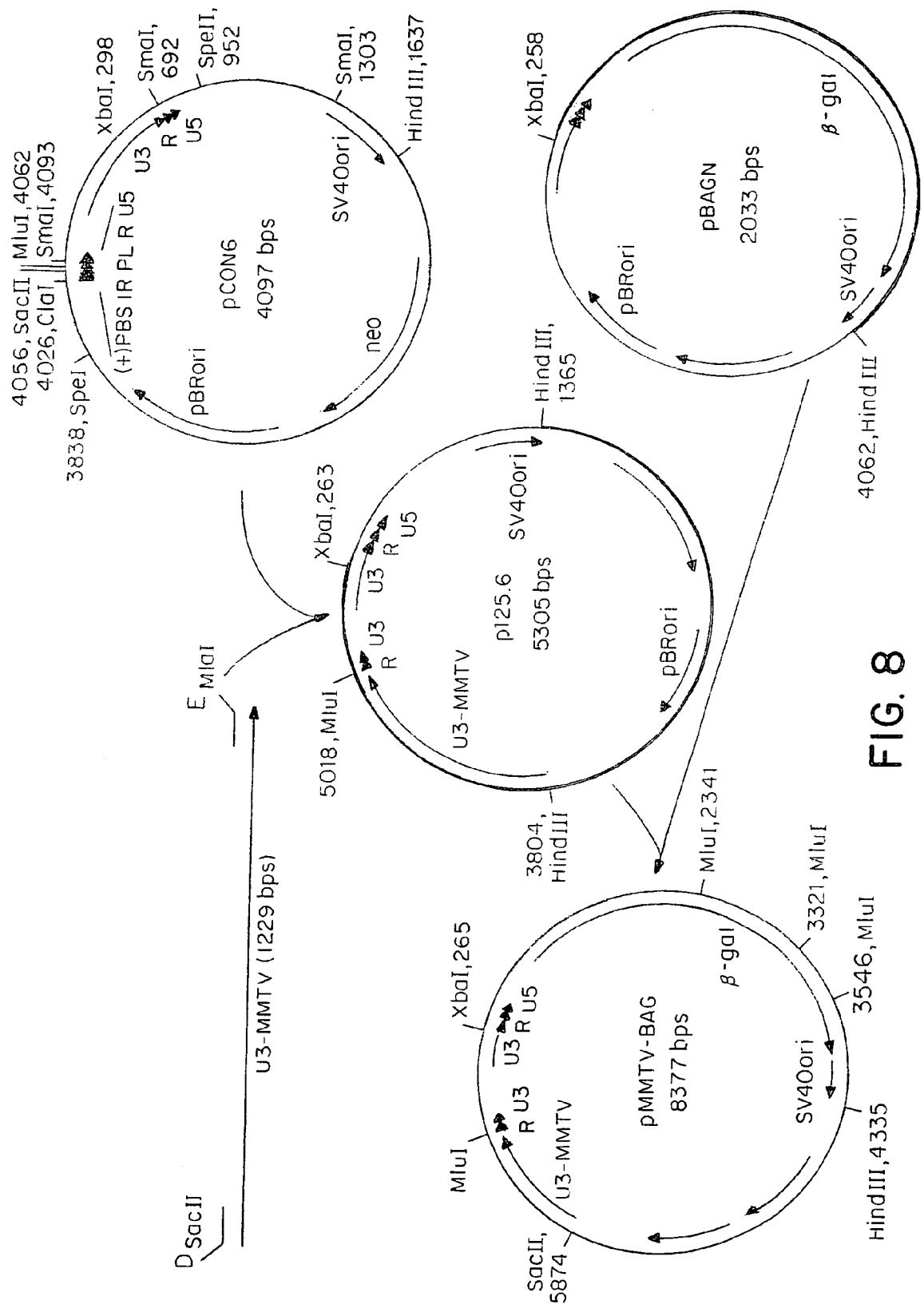
FIG. 8 is a graphic representation of construction of the plasmid pMMTV-BAG.

After 35 cycles of annealing at 49° C. and extension at 72° C., a 1229 bp product was obtained, digested with SacII and Mlul and ligated to the SacII/Mlul digested vector pCON6. The resulting plasmid p125.6 (5305 bp) (FIG. 8) was digested with XbaI and HindIII and the 4187 bp fragment ligated to the 4190 bp fragment of pBAGN containing the β-galactosidase gene to give the plasmid pMMTV-BAG (8377 bp) (FIG. 8) in which the β-galactosidase gene is under the transcriptional control of the MLV promoter after transfection, and under the MMTV promoter after infection.

Figure 10:
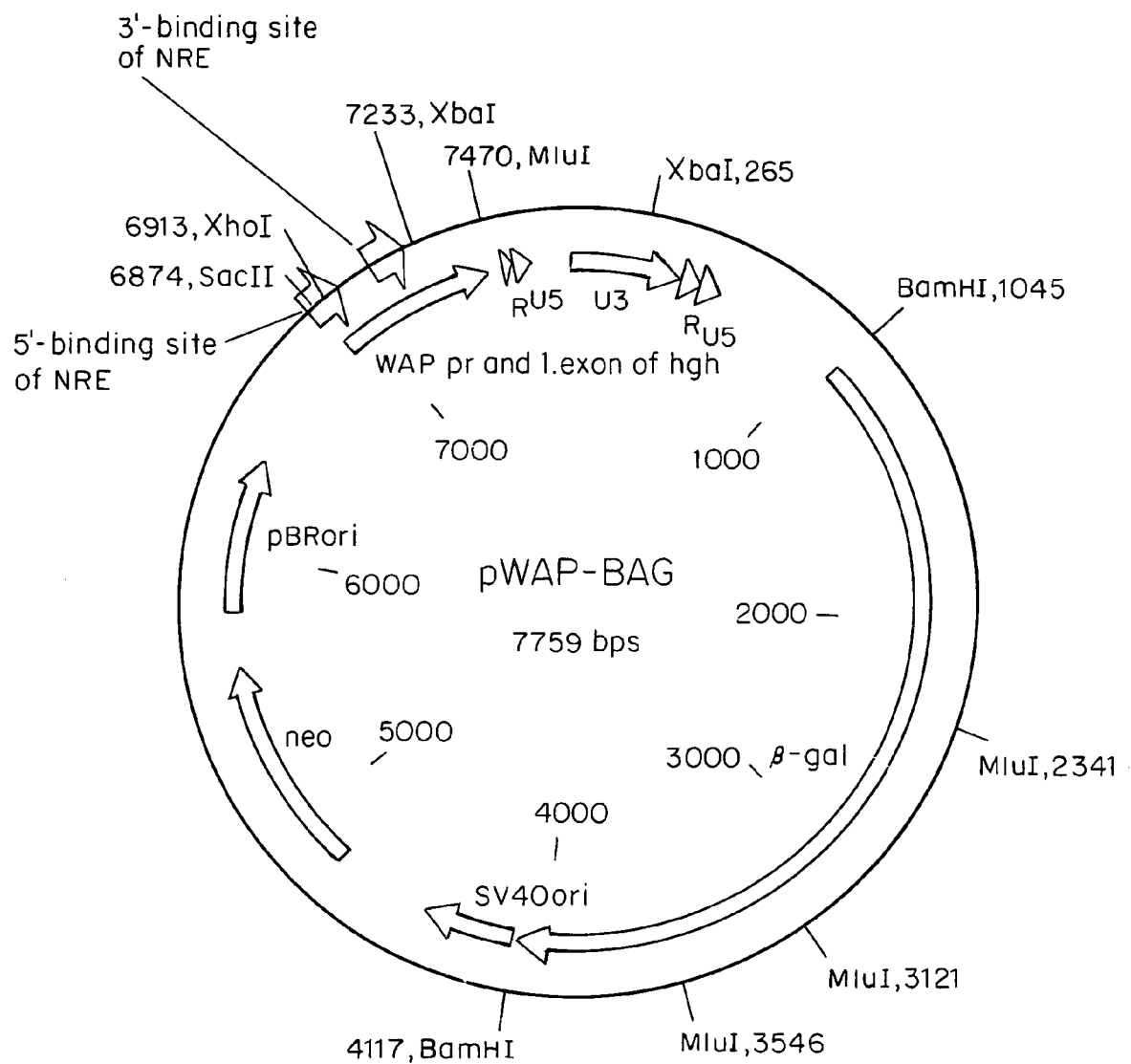
FIG. 10 is the plasmid pWAPBAG.

Cloning of the Whey Acidic Protein (WAP) Promoter Region Encompassing the Proximal 445 BP of the WAP Promoter Including the Transcription Initiation Site A plasmid, pWAPBAG containing the β-galactosidase gene under transcriptional control of the proximal 445 bp's of the WAP promoter was prepared by amplification of a sequence comprising the proximal 445 bp's of the WAP promoter and the first 143 bp's of the human growth hormone (HGH). The sequences were amplified from pWAP2-HGH (Günzburg et al., 1991) by PCR using primers F and G (FIG. 9). Both primers carried SacII and Mlul recognition sites as terminal sequences. The amplified 606 bp product and pCON6 were digested with SacII and Mlul and the 4094 bp fragment of the vector as well as the PCR product was ligated together to create pWAP.6. The β-galactosidase (β-gal) gene of *E. coli* was cloned into the resulting vector pWAP.6 (4687 bp): pWAP.6 as well as pBAGN were digested with BamHI and the linearised vector fragment as well as the 3072 bp β-gal fragment of pBAGN were ligated together. The resulting plasmid was pWAPBAG (FIG. 10), which is a ProCon vector in which the 3' 445 bp's containing the WAP-NRE, as well as the 5' 143 bp's of the HGH coding-sequence, were inserted in place of the U3 region in the 3'LTR.

The control of the β-galactosidase gene expression by promoters inserted into the polylinker has been validated by infection studies using the constructed MMTV and WAP retroviral vectors to infect various cells.

To produce retroviral vector particles, the MMTV and WAP ProCon vectors have been transfected into the packaging cell line GP+E86 (Markowitz et al., *J. Virol.* 62:1120-1124 (1988)). After selection for neomycin resistance, which is encoded by the vector, stable populations and clones of recombinant ProCon virus producing cells were obtained.

Virus containing supernatant from these populations was used to infect a mouse mammary cell line EF43 (Gunzburg et al., *Carcinogenesis* 9:1849-1856 (1988)) as well as a mouse fibroblast cell line (Jainchill et al., *J. Virol* 4:549-553 (1969)).

Figure 13:
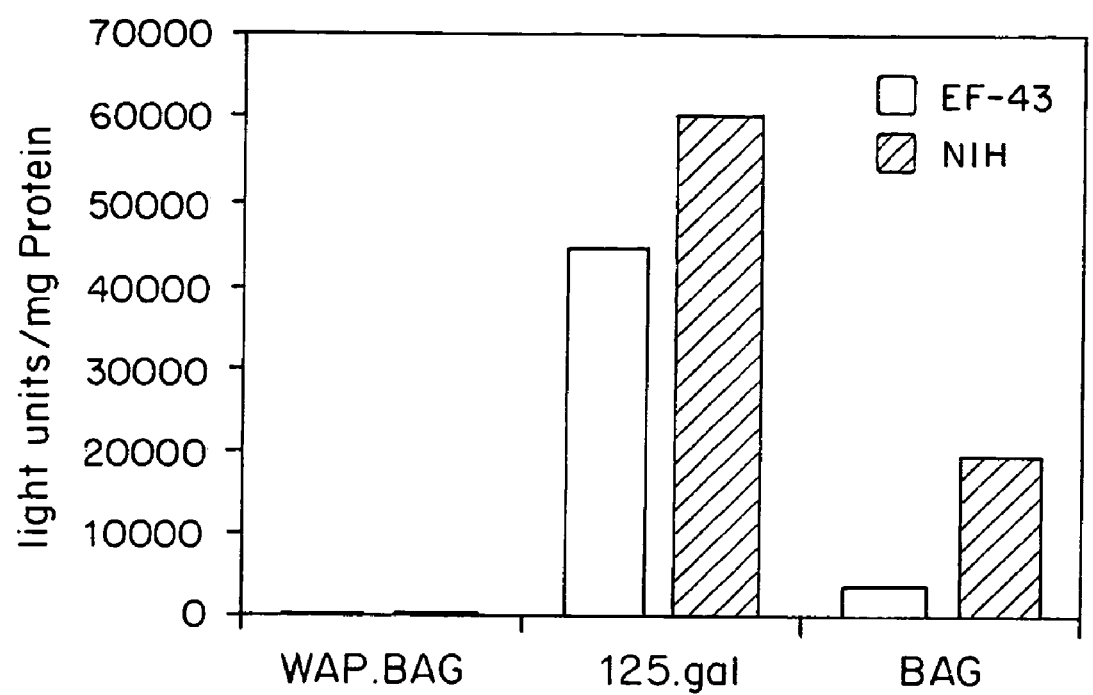
FIG. 13 is a graph of β-galactosidase expression in NIH and EF43 cells infected with MMTV and WAP ProCon vectors.
Figure 14:
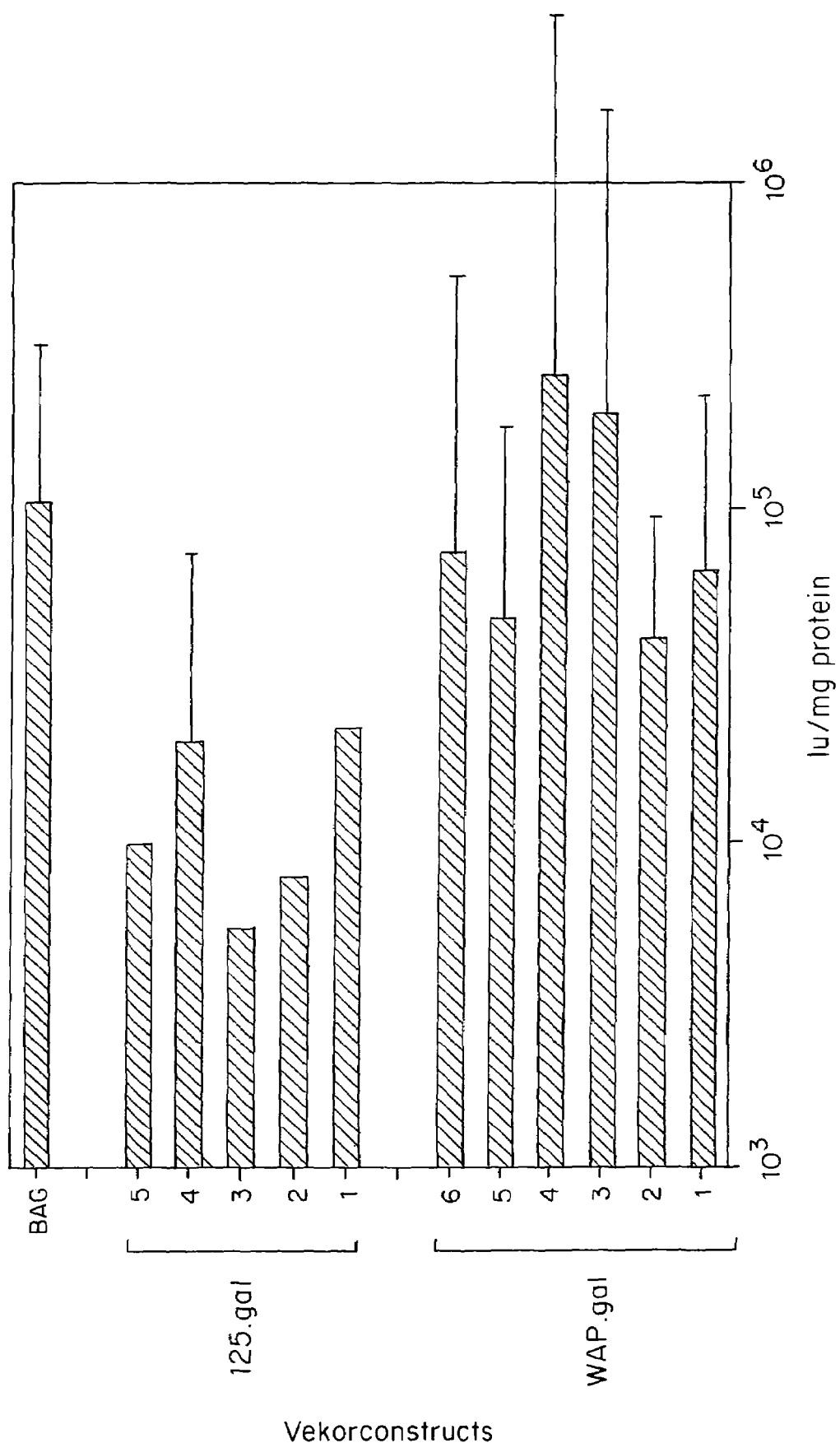
FIG. 14 is a graph of β-galactosidase expression in primary mammary glands cells from a pregnant mouse infected with MMTV and WAP ProCon vectors.
Figure 16:
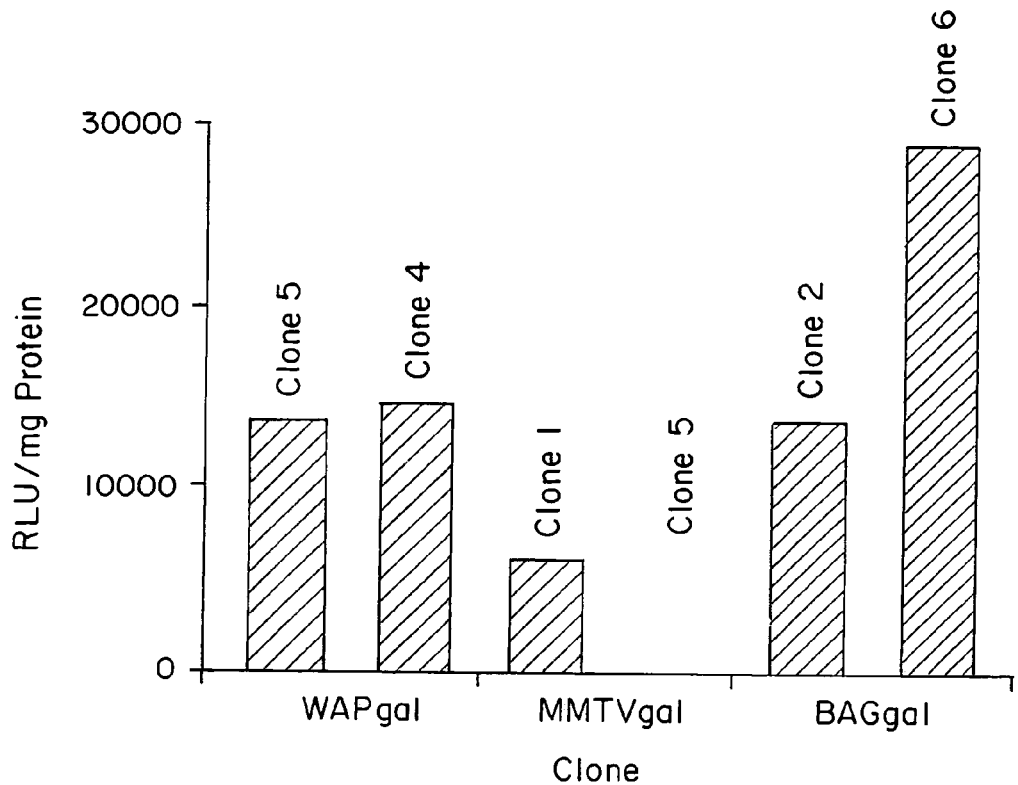
FIG. 16 is a graph of β-galactosidase expression in infected mammary tumor cells.

Four days after infection, the target cells were lysed and quantitative β-galactosidase assay revealed no expression in either cell type infected by the WAP carrying ProCon vectors and good expression in both cell types from the MMTV carrying ProCon vector (FIG. 13). This result is in accordance with the WAP promoter only functioning in vivo during late pregnancy and lactation and not in most simple in vitro mammary cell culture systems as represented by the EF43 cells. To investigate whether the WAP carrying ProCon vectors would be active in a complex primary mammary derived cell culture system, primary organoids from 8-10 day pregnant mice (FIG. 14) or from mammary tumors (FIG. 16) were taken into culture and infected with the supernatant from the same stably transfected population of transfected cell lines. Both ProCon vectors carrying the WAP and the MMTV promoter fragments were active in these primary cells (FIG. 14) and mammary tumor derived cells (FIG. 16) as demonstrated by β-galactosidese activity.

Figure 15:
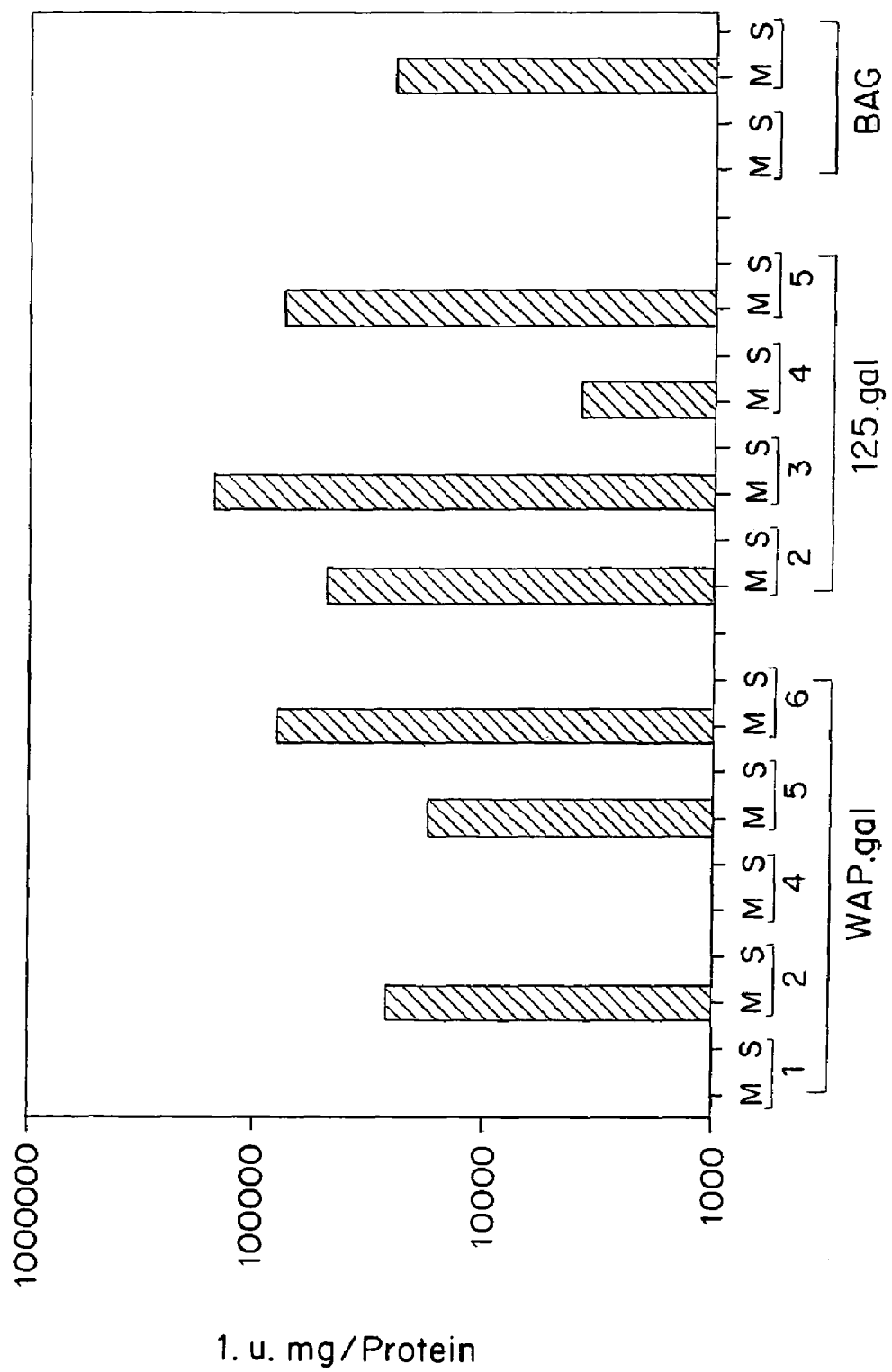
FIG. 15 is a graph of β-galactosidase expression after virus injection into mammary gland and the skin of a pregnant Balb/c mouse.

To investigate whether the WAP and MMTV carrying ProCon vectors were active in vivo and whether the expression of β-galactosidase was limited to the mammary gland in vivo, recombinant ProCon virus containing medium was injected in situ into the mammary glands or skin of 8-10 day pregnant mice. Five days later, the mice were sacrificed, cell extracts prepared and a β-galactosidase assay performed. Both the WAP and MMTV fragment carrying ProCon vectors were expressed only in the pregnant mammary gland and not in the skin (cf M and S in FIG. 15). Thus in vivo the regulatory elements from both promoters limit expression to the mammary gland whereas in vitro the regulatory elements from the WAP promoter retain their strict tissue specificity but those of MATV do not.

These ProCon vectors carrying tissues specific promoters and regulatory elements will be useful for directing the expression of therapeutic genes to predefined cell types, tissues and organs. Potential therapeutic genes include melittin, which has anti-HIV and anti-tumor effects, and genes which prime cells for death including the thymidine kinase, guanine phosphoribosytransferase and cytosine deaminase genes, cytochrome P450, as well as genes involved in cell cycle regulation such as SDI/WAF1/CIP-1.

EXAMPLE 2

Figure 11:
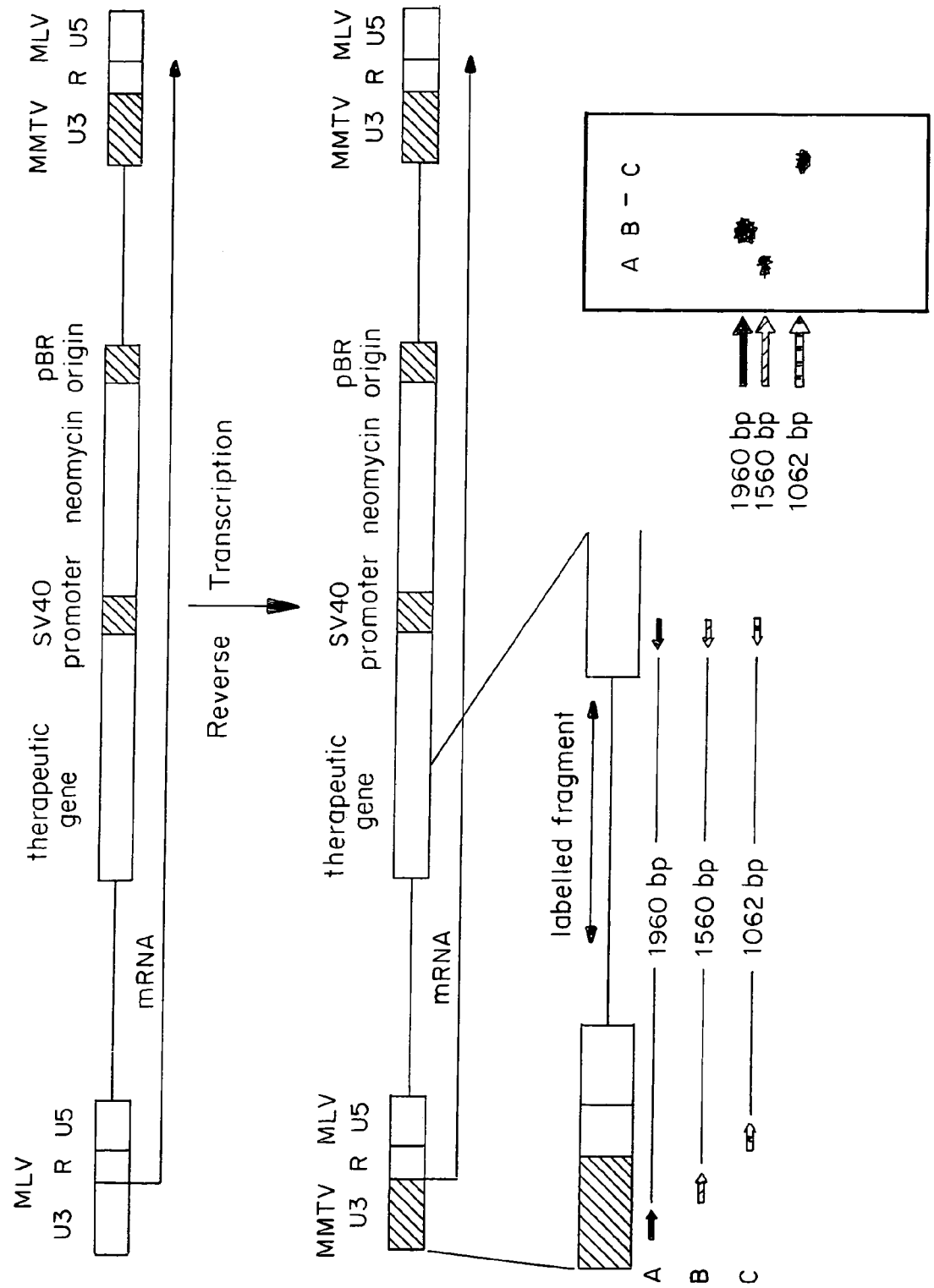
FIG. 11 is a graphic representation of a ProCon vector carrying the promoter region from a mouse mammary tumor (MMTV) and the results of PCR analysis of DNA, prepared from clones infected with the vector, using a MLV probe.
Figure 12:
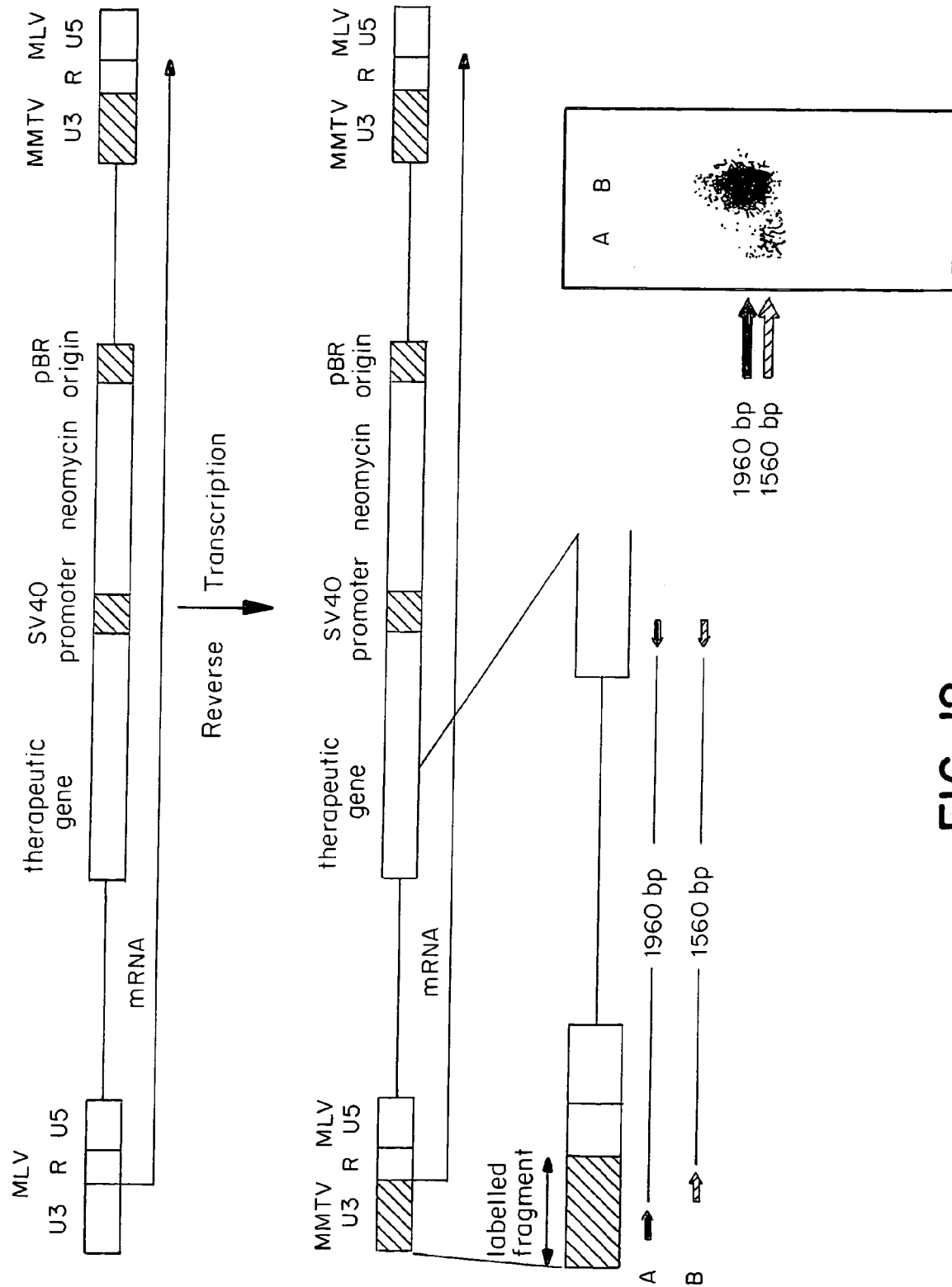
FIG. 12 is a graphic representation of a ProCon vector carrying the promoter region from a mouse mammary tumor (MMTV) and the results of PCR analysis of DNA, prepared from clones infected with the vector, using a MMTV probe.

Validation of Promoter Conversion in Cells Infected with a ProCon Vector that Originally Carried the MMTV Promoter in the 3'LTR A ProCon vector carrying the promoter region from mouse mammary tumor virus (MMTV) was transfected into a packaging cell line and the resultant recombinant vector particles used to infect an established human bladder carcinoma cell line (EJ). Infected cell clones were selected in medium carrying the neomycin analog G418 (since the vector carries a neomycin resistance gene driven from an internal SV40 promoter). DNA was prepared from one of the infected clones and nontransfected parental EJ cells and used for Polymerase Chain Reactions (PCR). The PCRs were performed using one of two primers that specifically recognize and bind to MMTV sequences (A, B in FIGS. 11 & 12) or the MLV R region (C in FIG. 11) of the LTR together with a primer located within the marker gene (FIGS. 11 & 12). Since the marker gene primer is only located down stream of the MMTV (or MLV R region) sequence if promoter conversion has occurred, a positive PCR signal obtained with the MMTV primers in combination with the marker gene primer is indicative of this. In FIG. 4 the PCR products using primers A, B or C are shown after hybridization to a labelled fragment from the MLV sequence, verifying that all three PCR products are of MLV origin. The size of the fragments verifies that promoter conversion has occurred. FIG. 5 shows the PCR products using primer A or B and hybdridized to an MMTV specific probe, again verifying that promoter conversion has occurred.

EXAMPLE 3

Construction of ProCon Vectors for Targeted Integration

Using the same BAG vector described in Example 1 above, a retroviral vector can be constructed in which a DNA sequence with homology to a cellular sequence can be inserted into the LTR. The resulting vector can be used to target the integration of either the homologous sequence inserted into the vector or the whole or part of the vectors into the homologous sequence present in the host cell genome.

Figure 17:
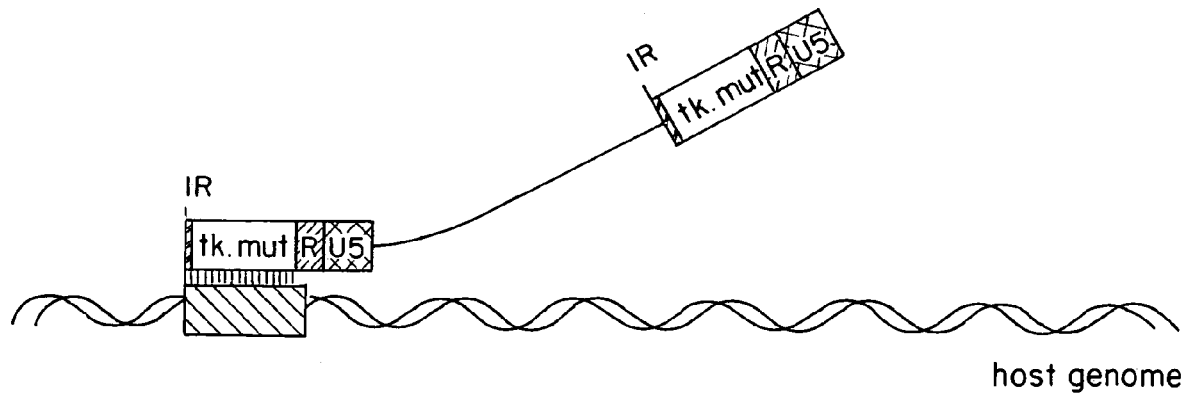
FIG. 17 is a graphic representation of targeted integration of a retroviral vector by homologous recombination.

According to the principle set forth above, a fragment of the thymidine kinase (tk) gene of herpes simplex virus (HSV) has been inserted into the polylinker region of the modified BAG vector (tk mutant in FIG. 17, Saller, R. M., "Design von Locus-und Gewebespezischen Retroviralen Vektoren Ruer Eine In Vivo Gentherapie, Doctoral thesis, Ludwigs-Maximilians University Munich, Germany, (1994)).

A cell line has also been established that has no functional copy of the mammalian tk gene and instead carries one copy of the HSV-tk gene (Saller, R. M., "Design von Locus-und Gewebespezischen Retroviralen Vektoren Ruer Eine In Vivo Gentherapie, Doctoral thesis, Ludwigs-Maximilians University Munich, Germany, (1994)). This cell line has been infected with the tk carrying BAG vector and cells that have undergone disruption of the HSV-tk gene have been selected (FIG. 17).

The above examples have illustrated the principles and consequences of the promoter conversion vectors provided by the present invention.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A retroviral vector which undergoes promoter conversion comprising in 5' to 3' order,
   (a) a 5' long terminal repeat region of the structure U3-R-U5;
   (b) one or more coding sequences, said sequences being inserted into the body of the vector; and
   (c) a 3' long terminal repeat region comprising a partially deleted U3 region into which a polylinker sequence containing a heterologous promoter has been inserted, wherein after infection of a target cell, said U3 of said 5' long terminal repeat region is replaced by said partially deleted U3 region and said heterologous promoter, resulting in said one or more coding sequences becoming operatively linked to said heterologous promoter and said heterologous promoter regulating expression of said one or more coding sequences in said target cell, and further wherein each long terminal repeat region is derived from a retrovirus selected from the group consisting of Murine Leukemia Virus, Mouse Mammary Tumor Virus, Murine Sarcoma Virus, Simian Immunodeficiency Virus, Human Immunodeficiency Virus, Human T Cell Leukemia Virus, Feline Immunodeficiency Virus, Feline Leukemia Virus, Bovine Leukemia Virus, Mason-Pfizer-Monkey Virus, and combinations thereof.

2. The retroviral vector according to claim 1, wherein said retroviral vector further comprises a regulatory element other than a promoter.

3. The retroviral vector according to claim 1, wherein said heterologous promoter is selected from the group consisting of: a Whey Acidic Protein specific promoter, a Mouse Mammary Tumor Virus specific promoter, β-lactoglobulin and casein specific promoters, a pancreas specific promoter, a lymphocyte specific promoter, a Mouse Mammary Tumor Virus specific promoter conferring responsiveness to glucocorticoid hormones or directing expression to the mammary gland, and combinations thereof.

4. The retroviral vector according to claim 1, wherein said retroviral vector is derived from a BAG vector.

5. The retroviral vector according to claim 1, wherein the coding sequences are selected from the group consisting of marker genes, therapeutic genes, antiviral genes, antitumor genes, cytokine genes and combinations thereof.

6. The retroviral vector according to claim 5, wherein said marker or therapeutic genes are selected from the group consisting of β-galactosidase gene, neomycin gene, Herpes Simplex Virus thymidine kinase gene, puromycin gene, cytosine deaminase gene, hygromycin gene, secreted alkaline phosphatase gene, guanine phosphoribosyl transferase (gpt) gene, alcohol dehydrogenase gene, hypoxanthine phosphoribosyl transferase (HPRT) gene and combinations thereof.

7. The retroviral vector according to claim 1, wherein at least one of said coding sequences is a retroviral coding sequence that is an altered or at least partially deleted retroviral gene.

8. The retroviral vector according to claim 1, wherein retroviral sequences involved in integration of retroviruses are altered or at least partially deleted.

9. The retroviral vector according to claim 1, wherein said vector comprises one or more sequences homologous to one or more cellular sequences or a part thereof.

10. The retroviral vector according to claim 2, wherein said regulatory element is regulatable by transacting molecules.

11. A retroviral vector kit comprising:
   (a) a retroviral vector which undergoes promoter conversion comprising in 5' to 3' order,
      (i) a 5' long terminal repeat region of the structure U3-R-U5;
      (ii) one or more coding sequences, said sequences being inserted into the body of the vector; and
      (iii) a 3' long terminal repeat region comprising a partially deleted U3 region into which a polylinker sequence containing a heterologous promoter has been inserted, wherein after infection of a target cell, said U3 of said 5' long terminal repeat region is replaced by said partially deleted U3 region and said heterologous promoter, resulting in said one or more coding sequences becoming operatively linked to said heterologous promoter and said heterologous promoter regulating expression of said one or more coding sequences in said target cell; and
   (b) a packaging cell line comprising one or more retroviral or recombinant retroviral constructs coding for those retroviral proteins required for said retroviral vector to be packaged which are not encoded in said retroviral vector.

12. The retroviral vector kit according to claim 11 wherein the packaging cell line is selected from the group consisting of psi-2, psi-Crypt, psi-AM, GP+E-86, PA317, and GP+envAM-12.

13. A recombinant retroviral particle obtained by transfecting a packaging cell line with a retroviral vector according to claim 1 and culturing the cells under suitable conditions.

14. A retroviral provirus produced by infecting a target cell with a recombinant retroviral particle according to claim 13, whereby the heterologous DNA fragment in the 3' long terminal repeat becomes duplicated during the process of reverse transcription in the target cell and appears in the 5' long terminal repeat as well as in the 3' long terminal repeat of the resulting provirus.

15. An mRNA molecule encoded by a retroviral provirus according to claim 14.

16. An RNA molecule encoded by a retroviral vector according to claim 1.

17. A pharmaceutical composition comprising a therapeutically effective amount of a recombinant retroviral particle according to claim 13.

18. A producer cell line producing a retroviral particle, the producer cell comprising a retroviral vector and a DNA construct coding for proteins required for the retroviral vector to be packaged, said retroviral vector comprising in 5' to 3' order,
   (a) a 5' long terminal repeat region of the structure U3-R-U5;
   (b) one or more coding sequences, said sequences being inserted into the body of the vector; and
   (c) a 3' long terminal repeat region comprising a partially deleted U3 region into which a polylinker sequence containing a heterologous promoter has been inserted, wherein after infection of a target cell, said U3 of said 5' long terminal repeat region is replaced by said partially deleted U3 region and said heterologous promoter, resulting in said one or more coding sequences becoming operatively linked to said heterologous promoter and said heterologous promoter regulating expression of said one or more coding sequences in said target cell, and further wherein each long terminal repeat region is derived from a retrovirus selected from the group consisting of Murine Leukemia Virus, Mouse Mammary Tumor Virus, Murine Sarcoma Virus, Simian Immunodeficiency Virus, Human Immunodeficiency Virus, Human T Cell Leukemia Virus, Feline Immunodeficiency Virus, Feline Leukemia Virus, Bovine Leukemia Virus, Mason-Pfizer-Monkey Virus, and combinations thereof.

19. A recombinant retroviral particle comprising a genome encoded by a retroviral vector according to claim 1.

20. The retroviral vector according to claim 1, wherein said promoter is target cell specific in its expression.

21. The retroviral vector according to claim 2, wherein said regulatory element is target specific in its expression.

22. A retroviral vector which undergoes promoter conversion comprising in 5' to 3' order,
   (a) a 5' long terminal repeat region of the structure U3-R-U5;
   (b) one or more coding sequences, said sequences being inserted into the body of the vector; and
   (c) a 3' long terminal repeat region comprising a partially deleted U3 region into which a polylinker sequence containing a promoter from a cellular gene has been inserted,
   wherein after infection of a target cell, said U3 of said 5' long terminal repeat region is replaced by said partially deleted U3 region and said promoter from a cellular gene, resulting in said one or more coding sequences becoming operatively linked to said promoter from a cellular gene and said promoter from a cellular gene regulating expression of said one or more coding sequences in said target cell, and further wherein each long terminal repeat region is derived from a retrovirus selected from the group consisting of Murine Leukemia Virus, Mouse Mammary Tumor Virus, Murine Sarcoma Virus, Simian Immunodeficiency Virus, Human Immunodeficiency Virus, Human T Cell Leukemia Virus, Feline Immunodeficiency Virus, Feline Leukemia Virus, Bovine Leukemia Virus, Mason-Pfizer-Monkey Virus, and combinations thereof.

23. The retroviral vector according to claim 22, wherein said vector further comprises a regulatory element other than a promoter.

24. The retroviral vector according to claim 22, wherein said promoter is selected from the group consisting of: a Whey Acidic Protein promoter, β-lactoglobulin and casein specific promoters, a pancreas specific promoter, lymphocyte specific promoters, and combinations thereof.

25. The retroviral vector according to claim 22, wherein said retroviral vector is derived from a BAG vector.

26. The retroviral vector according to claim 22, wherein the coding sequences are selected from the group consisting of marker genes, therapeutic genes, antiviral genes, antitumor genes, cytokine genes and combinations thereof.

27. The retroviral vector according to claim 26, wherein said marker or therapeutic genes are selected from the group consisting of β-galactosidase gene, neomycin gene, Herpes Simplex Virus thymidine kinase gene, puromycin gene, cytosine deaminase gene, hygromycin gene, secreted alkaline phosphatase gene, guanine phosphoribosyl transferase (gpt) gene, alcohol dehydrogenase gene, hypoxanthine phosphoribosyl transferase (HPRT) gene and combinations thereof.

28. The retroviral vector according to claim 22, wherein at least one of said coding sequences is a retroviral coding sequence that is an altered or at least-partially deleted retroviral gene.

29. The retroviral vector according to claim 22, wherein retroviral sequences involved in integration of retroviruses are altered or at least partially deleted.

30. The retroviral vector according to claim 22, wherein said promoter is regulatable by transacting molecules.

31. A retroviral vector kit comprising:
  (a) a retroviral vector which undergoes promoter conversion comprising in 5' to 3' order,
    (i) a 5' long terminal repeat region of the structure U3-R-U5;
    (ii) one or more coding sequences, said sequences being inserted into the body of the vector; and
    (iii) a 3' long terminal repeat region comprising a partially deleted U3 region into which a polylinker sequence containing a promoter from a cellular gene has been inserted, wherein after infection of a target cell, said U3 of said 5' long terminal repeat region is replaced by said partially deleted U3 region and said promoter from a cellular gene, resulting in said one or more coding sequences becoming operatively linked to said promoter from a cellular gene and said promoter from a cellular gene regulating expression of said one or more coding sequences in said target cell; and
  (b) a packaging cell line comprising one or more retroviral or recombinant retroviral constructs coding for those retroviral proteins required for said retroviral vector to be packaged which are not encoded in said retroviral vector.

32. The retroviral vector kit according to claim 31, wherein the packaging cell line is selected from the group consisting of psi-2, psi-Crypt, psi-AM, GP+E-86, PA317, and GP+envAM-12.

33. A recombinant retroviral particle obtained by transfecting a packaging cell line with a retroviral vector according to claim 22 and culturing the cells under suitable conditions.

34. A retroviral provirus produced by infecting a target cell with a recombinant retroviral particle according to claim 33, whereby the promoter in the 3' long terminal repeat becomes duplicated during the process of reverse transcription in the target cell and appears in the 5' long terminal repeat as well as in the 3' long terminal repeat of the resulting provirus.

35. An mRNA molecule encoded by a retroviral provirus according to claim 34.

36. An RNA molecule encoded by a retroviral vector according to claim 22.

37. A pharmaceutical composition comprising a therapeutically effective amount of a recombinant retroviral particle according to claim 33.

38. A producer cell line producing a retroviral particle, the producer cell comprising a retroviral vector and a DNA construct coding for proteins required for the retroviral vector to be packaged, said retroviral vector comprising in 5' to 3' order,
  (a) a 5' long terminal repeat region of the structure U3-R-U5;
  (b) one or more coding sequences, said sequences being inserted into the body of the vector; and
  (c) a 3' long terminal repeat region comprising a partially deleted U3 region into which a polylinker sequence containing a promoter from a cellular gene has been inserted,
  wherein after infection of a target cell, said U3 of said 5' long terminal repeat region is replaced by said partially deleted U3 region and said promoter from a cellular gene, resulting in said one or more coding sequences becoming operatively linked to said promoter from a cellular gene and said promoter from a cellular gene regulating expression of said one or more coding sequences in said target cell, and further wherein each long terminal repeat region is derived from a retrovirus selected from the group consisting of Murine Leukemia Virus, Mouse Mammary Tumor Virus, Murine Sarcoma Virus, Simian Immunodeficiency Virus, Human Immunodeficiency Virus, Human T Cell Leukemia Virus, Feline Immunodeficiency Virus, Feline Leukemia Virus, Bovine Leukemia Virus, Mason-Pfizer-Monkey Virus, and combinations thereof.

39. A method for introducing homologous or heterologous nucleotide sequences into cells in an animal or cultured cells, said method comprising infecting the cells with a recombinant retrovirus produced by the producer cell line of claim 38.

40. The method according to claim 39, wherein the nucleotide sequences are selected from the group consisting of genes or parts of genes encoding for proteins, regulatory sequences and promoters and combinations thereof.

41. A recombinant retroviral particle comprising a genome encoded by a retroviral vector according to claim 22.

42. The retroviral vector according to claim 22, wherein said promoter is target cell specific in its expression.

43. A retroviral vector which undergoes promoter conversion comprising in 5' to 3' order,
  (a) a 5' long terminal repeat region of the structure U3-R-U5;
  (b) one or more coding sequences, said sequences being inserted into the body of the vector; and
  (c) a 3' long terminal repeat region comprising a partially deleted U3 region into which a polylinker sequence containing a heterologous retroviral promoter has been inserted, wherein after infection of a target cell, said U3 of said 5' long terminal repeat region is replaced by said partially deleted U3 region and said heterologous retroviral promoter, resulting in said one or more coding sequences becoming operatively linked to said heterologous retroviral promoter and said heterologous retroviral promoter regulating expression of said one or more coding sequences in said target cell, and further wherein each long terminal repeat region is derived from a retrovirus selected from the group consisting of Murine Leukemia Virus, Mouse Mammary Tumor Virus, Murine Sarcoma Virus, Simian Immunodeficiency Virus, Human Immunodeficiency Virus, Human T Cell Leukemia Virus, Feline Immunodeficiency Virus, Feline Leukemia Virus, Bovine Leukemia Virus, Mason-Pfizer-Monkey Virus, and combinations thereof.

44. The retroviral vector according to claim 43, wherein said vector further comprises a regulatory element other than a promoter.

45. The retroviral vector according to claim 43, wherein said promoter is selected from the group consisting of a Mouse mammary Tumor specific promoter, a Mouse Mammary Tumor Virus specific promoter conferring responsiveness to glucocorticoid hormones or directing expression to the mammary gland, and combinations thereof.

46. The retroviral vector according to claim 43, wherein said retroviral vector is derived from a BAG vector.

47. The retroviral vector according to claim 43, wherein the coding sequences are selected from the group consisting of marker genes, therapeutic genes, antiviral genes, antitumor genes, cytokine genes and combinations thereof.

48. The retroviral vector according to claim 47, wherein said marker or therapeutic genes are selected from the group consisting of β-galactosidase gene, neomycin gene, Herpes Simplex Virus thymidine kinase gene, puromycin gene, cytosine deaminase gene, hygromycin gene, secreted alkaline phosphatase gene, guanine phosphoribosyl transferase (gpt) gene, alcohol dehydrogenase gene, hypoxanthine phosphoribosyl transferase (HPRT) gene and combinations thereof.

49. The retroviral vector according to claim 43, wherein at least one of said coding sequences is a retroviral coding sequence that is an altered or at least partially deleted retroviral gene.

50. The retroviral vector according to claim 43, wherein retroviral sequences involved in integration of retroviruses are altered or at least partially deleted.

51. The retroviral vector according to claim 43, wherein said promoter is regulatable by transacting molecules.

52. A retroviral vector kit comprising:
(a) a retroviral vector which undergoes promoter conversion comprising in 5' to 3' order,
(i) a 5' long terminal repeat region of the structure U3-R-U5;
(ii) one or more coding sequences, said sequences being inserted into the body of the vector; and
(iii) a 3' long terminal repeat region comprising a partially deleted U3 region into which a polylinker sequence containing a heterologous retroviral promoter has been inserted, wherein after infection of a target cell, said U3 of said 5' long terminal repeat region is replaced by said partially deleted U3 region and said heterologous retroviral promoter, resulting in said one or more coding sequences becoming operatively linked to said heterologous retroviral promoter and said heterologous retroviral promoter regulating expression of said one or more coding sequences in said target cell; and (b) a packaging cell line harboring one or more retroviral or recombinant retroviral constructs coding for those retroviral proteins required for said retroviral vector to be packaged which are not encoded in said retroviral vector.

53. The retroviral vector kit according to claim 52, wherein the packaging cell line is selected from the group consisting of psi-2, psi-Crypt, psi-AM, GP+E-86, PA317, and GP+envAM-12.

54. A recombinant retroviral particle obtained by transfecting a packaging cell line with a retroviral vector according to claim 43 and culturing the cells under suitable conditions.

55. A retroviral provirus produced by infecting a target cell with a recombinant retroviral particle according to claim 54, whereby the promoter in the 3' long terminal repeat becomes duplicated during the process of reverse transcription in the target cell and appears in the 5' long terminal repeat as well as in the 3' long terminal repeat of the resulting provirus.

56. An mRNA molecule encoded by a retroviral provirus according to claim 55.

57. An RNA molecule encoded by a retroviral vector according to claim 53.

58. A pharmaceutical composition comprising a therapeutically effective amount of a recombinant retroviral particle according to claim 54.

59. A producer cell line producing a retroviral particle, the producer cell comprising a retroviral vector and a DNA construct coding for proteins required for the retroviral vector to be packaged, said retroviral vector comprising in 5' to 3' order,
(a) a 5' long terminal repeat region of the structure U3-R-U5;
(b) one or more coding sequences, said sequences being inserted into the body of the vector; and
(c) a 3' long terminal repeat region comprising a partially deleted U3 region into which a polylinker sequence containing a heterologous retroviral promoter has been inserted,
wherein after infection of a target cell, said U3 of said 5' long terminal repeat region is replaced by said partially deleted U3 region and said heterologous retroviral promoter, resulting in said one or more coding sequences becoming operatively linked to said heterologous retroviral promoter and said heterologous retroviral promoter regulating expression of said one or more coding sequences in said target cell, and further wherein each long terminal repeat region is derived from a retrovirus selected from the group consisting of Murine Leukemia Virus, Mouse Mammary Tumor Virus, Murine Sarcoma Virus, Simian Immunodeficiency Virus, Human Immunodeficiency Virus, Human T Cell Leukemia Virus, Feline Immunodeficiency Virus, Feline Leukemia Virus, Bovine Leukemia Virus, Mason-Pfizer-Monkey Virus, and combinations thereof.

60. A method for introducing homologous or heterologous nucleotide sequences into cells in an animal or cultured cells, said method comprising infecting the cells with a recombinant retrovirus produced by the producer cell line of claim 59.

61. The method according to claim 60, wherein the nucleotide sequences are selected from the group consisting of genes or parts of genes encoding for proteins, regulatory sequences and promoters and combinations thereof.

62. A recombinant retroviral particle comprising a genome encoded by a retroviral vector according to claim 43.

63. The retroviral vector according to claim 43, wherein said promoter is target cell specific in its expression.

64. A method for introducing homologous or heterologous nucleotide sequences into cells in an animal or cultured cells, said method comprising infecting the cells with a recombinant retrovirus produced by the producer cell line of claim 18.

65. The method according to claim 64, wherein the nucleotide sequences are selected from the group consisting of genes or parts of genes encoding for proteins, regulatory sequences and promoters and combinations thereof.

* * * * *

UNITED STATES PATENT AND TRADEMARK OFFICE
CERTIFICATE OF CORRECTION

PATENT NO. : 7,531,353 B1  Page 1 of 1
APPLICATION NO. : 08/808827
DATED : May 12, 2009
INVENTOR(S) : Gunzburg and Saller It is certified that error appears in the above-identified patent and that said Letters Patent is hereby corrected as shown below:

On title page, item 73 Assignee replace "GSF-Forschungszentrum fuer Umwelt und Gesundheit GmbH"
with -- Helmholtz Zentrum München Deutsches Forschungszentrum für Gesundheit und Umwelt (GmbH) --.

Signed and Sealed this

First Day of June, 2010

David J. Kappos
*Director of the United States Patent and Trademark Office*

```
                         SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:1:

ATGAAAGACC CCGCGGACGC GTGCGCCAGT CCTCCGATTG A                           41

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:2:

TCAATCACTC AGAGGAGACC                                                   20

(2) INFORMATION FOR SEQ ID NO:3:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:3:
```

```
ACATCGATAG AAAAAGGGGG GAATGAAAGA CCCCGCGGAC G                              41

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

ATACCGCGGA AAAGGGGGA AATGCC                                               26

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GCGGCGACGC GTAAGTTTAC TCAAAAAATC AGC                                      33

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

AACCGCGGCC AGGAGAAGTC ACCCTCAG                                            28

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

ACACGCGTCT GCCTCTCCCC TCAGGACACA                                          30
```